United States Patent
Grueb et al.

(10) Patent No.: US 11,635,438 B2
(45) Date of Patent: Apr. 25, 2023

(54) IL-6 DETECTION BASED EARLY DIAGNOSIS AND PREDICTION OF SYSTEMIC INFLAMMATORY RESPONSE SYNDROME AND SEPSIS IN ASYMPTOMATIC PATIENTS

(71) Applicants: Roche Diagnostics Operations, Inc., Indianapolis, IN (US); Medizinische Universität Graz, Graz (AT)

(72) Inventors: Susanne Grueb, Lucerne (CH); Nicole Neuboeck, Graz (AT); Freyja-Maria Smolle-Juettner, Graz (AT); Annelie-Martina Weinberg, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 137 days.

(21) Appl. No.: 15/196,718

(22) Filed: Jun. 29, 2016

(65) Prior Publication Data
US 2016/0305957 A1 Oct. 20, 2016

Related U.S. Application Data

(60) Division of application No. 13/601,787, filed on Aug. 31, 2012, now abandoned, which is a continuation of application No. PCT/EP2011/001006, filed on Mar. 2, 2011.

(30) Foreign Application Priority Data

Mar. 2, 2010 (EP) ..................... 10002190

(51) Int. Cl.
*G01N 33/53* (2006.01)
*G01N 33/68* (2006.01)

(52) U.S. Cl.
CPC . *G01N 33/6869* (2013.01); *G01N 2333/5412* (2013.01); *G01N 2800/24* (2013.01); *G01N 2800/26* (2013.01); *G01N 2800/50* (2013.01)

(58) Field of Classification Search
CPC .......... G01N 33/6869; G01N 2800/24; G01N 2800/50; G01N 2333/5412; G01N 2800/26
See application file for complete search history.

(56) References Cited

U.S. PATENT DOCUMENTS

| 5,744,305 | A | 4/1998 | Fodor et al. |
| 5,882,872 | A | 3/1999 | Kudsk |
| 2008/0114576 | A1 | 5/2008 | Jackson et al. |

FOREIGN PATENT DOCUMENTS

| CN | 101393204 A | 3/2009 |
| EP | 0430193 A1 | 11/1990 |
| EP | 1835283 A1 | 9/2007 |
| JP | 2009-229340 A | 10/2009 |

OTHER PUBLICATIONS

Yajima et al. (Bull.Tokio dent,Coll 2000;vol. 41,No. 4,pp. 187-194).*
Fraunberger et al., (Clin Chem Lab Med 1998; 36(10):797-801).*
Lehrke et al., (Critical Care 2008; 12:R157, pp. 1-80).*
Giannoudis et al., J.Trauma 2008;65:646-652.*
BE-8 abcam(1998, retrieved from https://www.abcam.com/il-6-antibody-b-e8-ab11449-references.html#top-274).*
IL-6 ELISA Reference Guide and Catalog (2008;R&D, retrieved from http://www.woongbee.com/0NewHome/RnD/ELISA_main_HA/main_link/ELISA_reference_guide.pdf).*
Giannoudis et al., "Correlation Between IL-6 Levels and the Systemic Inflammatory Response Score: Can an IL-6 Cutoff Predict a SIRS State?" J.Trauma 2008;65:646-652 (Year: 2008).*
Invitrogen Mouse (monocional) Anti-Human Interleukin-6 Biotin Conjugate Product Analysis Sheet, Diaclone SAS, 2013, p. 5.
Rittirsch, D., et al., "The disconnect between animal models of sepsis and human sepsis," Joural of Leukocyte Biology, Jan. 2007, pp. 137-143, vol. 81.
Drucker. Claudia et al.. "Impact of interleukin-6 classic-and trans-signaling on liver damage and regeneration," Journal of Autoimmunity, 2010, pp. 29-37, vol. 34.
Garibotto, Giacomo et al., "Kidney and splanchnic handling of Interleukin-6 in humans," Cytokine, 2007, pp. 51-54, vol. 37.
Goldstein, Brahm et al., "International pediatric sepsis consensus conference: Definitions for sepsis and organ dysfunction in pediatrics," Pediatric Critical Care Medicine, 2005, pp. 2-8, vol. 6, No. 1.
Hanley, James A. and McNeil, Barbara J., "The Meaning and Use of the Area under a Receiver Operating Characteristic (ROC) Curve," Radiology, Apr. 1982, pp. 29-36, vol. 143.
Hodgin, Katherine E. and Moss, Marc, "The Epidemiology of Sepsis," Current Pharmaceutical Design, 2008, pp. 1833-1839, vol. 14.
Klein, Bernard et al., "Murine Anti-Interleukin-6 Monoclonal Antibody Therapy for a Patient With Plasma Cell Leukemia," Blood, 1991, pp. 1198-1204, vol. 78, No. 5.

(Continued)

*Primary Examiner* — Carmencita M Belei
(74) *Attorney, Agent, or Firm* — Stinson LLP

(57) ABSTRACT

Methods, systems and kits for the early diagnosis or prediction of systemic inflammatory response syndrome (SIRS) including sepsis in asymptomatic patients, such as patients undergoing a surgical intervention, are provided. Some embodiments include a method and system for the detection or diagnosis of SIRS, or detection or diagnosis of a risk to suffer from or develop SIRS, in an asymptomatic patient comprising the steps of determining the level of IL-6 (or a variant thereof) in a sample from the patient; comparing the level of IL-6 (or a variant thereof) to a reference level; detecting or diagnosing SIRS or diagnosing a risk to suffer from or develop SIRS, wherein the sample is isolated at least 2 times at short intervals and the determining and comparing steps are both repeated for each sample. Also provided are methods, systems and kits for therapy monitoring and mortality prediction.

6 Claims, 20 Drawing Sheets
Specification includes a Sequence Listing.

(56) References Cited

OTHER PUBLICATIONS

Kobold, Uwe et al., "Quantification of Hepcidin-25 in Human Serum by Isotope Dilution Micro-HPLC-Tandem Mass Spectrometry," Clinical Chemistry, 2008, pp. 1584-1586, vol. 54, No. 9.
NCBI Reference Sequence NP 000591.1, "Interleukin-6 precursor [*Homo sapiens*]", 5 pages.
Needleman, Saul B. and Wunsch, Christian D., "A General Method Applicable to the Search for Similarities in the Amino Acid Sequence of Two Proteins," Journal of Molecular Biology, 1970, pp. 443-453, No. 48.
Nolan, John P. and Sklar, Larry A., "Suspension array technology: evolution of the flat-array paradigm," Trends in Biotechnology, Jan. 2002, pp. 9-12, vol. 20, No. 1.
Pearson, William R. and Lipman, David J., "Improved tool for biological and sequence comparison," Proceedings 0 the National Academy of Sciences USA, Apr. 1988, pp. 2444-2448, vol. 85.
Smith, Temple F. and Waterman, Michael S., "Comparison of Biosequence," Advances in Applied Mathematics, 1981, pp. 482-489, vol. 2.
Song, Mingchen and Kellum, John A., "Interleukin-6," Critical Care Medicine, 2005, pp. S463-S465, vol. 33, No. 12 (Supplement).
Taga, Tetsuya and Kishimoto, Tadamitsu, "GP130 and the Interleukin-6 Family of Cytokines," Annual Review of Immunology, 1997, pp. 797-819, vol. 15.
American College of Chest Physicians/Society of Critical Care Medicine Consensus Conference: Definitions for sepsis and organ failure and guidelines for the use of innovative therapies in sepsis, Critical Care Medicine, 1992, pp. 864-874, vol. 20, No. 6.
Bender, L. et al., "Early and late markers for the detection of early-onset neonatal sepsis," Danish Medical Bulletin, Nov. 2008, pp. 219-223, vol. 55, No. 4.
Billeter, Adrian et al., Early Serum Procalcitonin, Interleukin-6, and 24-Hour Lactate Clearance: Useful Indicators of Septic Infections in Severely Traumatized Patients, World Journal of Surgery, 2009, pp. 558-566, vol. 33, No. 3.
Diepold, Miriam et at., "Performance of Interleukin-6 and Interleukin-8 serum levels in pediatric oncology patients with neutropenia and fever for the assessment of low-risk," BMC Infectious Diseases, 2008, 7 pages, vol. 8, No. 28.
Hamalainen, Sari et al., "Severe sepsis in autologous stem cell transplant recipients: Microbiological aetiology, risk factors and outcome," Scandinavian Journal of Infectious Diseases, 2009, pp. 14-20, vol. 41.
Gumanenko, E. K. et al., "C-reactive protein in severe combined trauma not complicated and complicated by sepsis," Medline/NLM16768340, printed Jan. 25, 2011, 1 page, English abstract.
Kuester, Helmut et al., "Interleukin-1 receptor antagonist and interleukin-6 for early diagnosis of neonatal sepsis 2 days before clinical manifestation," The Lancet, Oct. 17, 1998, pp. 1271-1277, vol. 352.
Mathai, Elizabeth et al., "Is C-Reactive Protein Level Useful in Differentiating Infected from Uninfected Neonates Among Those at Risk of Infection?" Indian Pediatrics, Sep. 17, 2004, pp. 895-900, vol. 41.
Mokart, D. et al., "Early postoperative compensatory anti-inflammatory response syndrome is associated with septic complications after major surgical trauma in patients with cancer," British Journal of Surgery, 2002, pp. 1450-1456, vol. 89.
Mokart, D. et al., "Procalcitonin, interleukin 6 and systemic inflammatory response syndrome (SIRS): early markers of postoperative sepsis after major surgery," British Journal of Anesthesia, 2005, pp. 767-773, vol. 94, No. 6.
Prinsen, J. H. et al., "Interleukin-6 as diagnostic marker for neonatal sepsis: determination of Access IL-6 cutoff for newborns," Information & Retrievel Services SO-II, printed Jun. 25, 2009, 2 pages, Abstract.
Redl, Heinz et al., "Procalcitonin release patterns in a baboon model of trauma and sepsis: Relationship to cytokines and neopterin," Critical Care Medicine, Nov. 2000, pp. 3659-3663, vol. 28, No. 11.
Jones, et al., The systemic inflammatory response syndrome as a predictor of bacteraemia and outcome from sepsis, 1996, vol. 89, pp. 515-522.
Mayeux, R., Biomarkers: Potential Uses and Limitations, vol. 1, No. 2, pp. 182-188.
Brailly, et al., Total Interleukin-6 in Plasma Measured by Immunoassay, 1994, Immunology, vol. 40, No. 1, pp. 116-123.
Lehrke, et al., Serum concentration of cortisol, interleukin 6, leptin and adiponectin predict stress induced insulin resistance in acute inflammattory reactions, 2008, Crit Care, vol. 12, No. 6, R157.
Brown, et al., Tolerance of single, but not multiple, amino acid replacements in antibody VH CDR 2: a means of minimizing B cell wastage from somatic hypermutation?, 1996, The Journal of Immunology, vol. 156, No. 9, pp. 3285-3291.
Vajdos, et al., Comprehensive Functional Maps of the Antigen-binding Site of an Anti-ErbB2 Antibody Obtained with Shotgun Scanning Mutagenesis, Journal of Molecular Biology, vol. 320, No. 2, 2002, pp. 415-428.
Ellstrom et al., Evaluation of Tissue Trauma After Laparoscopic And Abdominal hysterectomy: Measurements of Neutrophil Activation and Release of Interleukin-6, Cortisol, And C-reactive Protein; Journal of the American College of Surgeons, May 1996, vol. 182, pp. 423-430.
Kawakami et al., Measurement of interleukin-6, interleukin-10, and tumor necrosis factor-alpha levels in tissues and plasma after thermal injury in mice; Department of Traumatology and Critical Care Medicine, National Defense Medical College, Saitama, Japan; Surgery; vol. 121, No. 4, pp. 440-448.
Kumbhaare et al., Injury Measurement Properties of Serum Interleukin-6 Following Lumbar Decompression Surgery; Journal of Surgical Research, 2009, vol. 157, No. 2, pp. 161-167.
Mackinnon, Laurel T.; Advances in Exercise Immunology, The University of Queensland, Australia; 10 pages.

\* cited by examiner

IL-6 (pg/ml) kinetics in un-symptomatic patients pre- and post-surgery. Comparison between patients who develop SIRS/sepsis and those who don't.

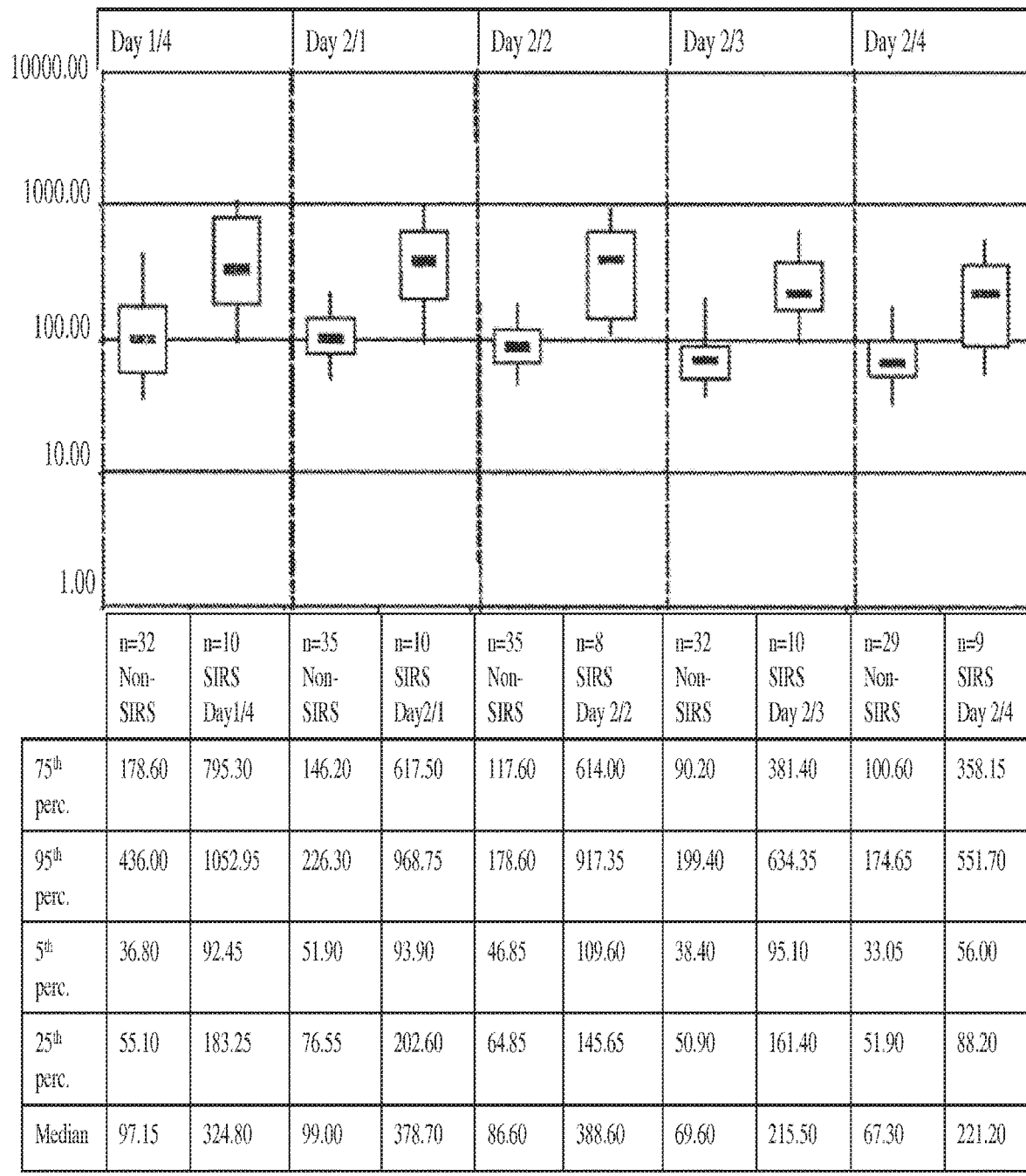

IL-6 (pg/ml) kinetics in un-symptomatic patients pre- and post-surgery. Comparison between patients who develop SIRS/sepsis and those who don't.

IL-6 (pg/ml) kinetics in un-symptomatic patients pre- and post-surgery. Comparison between patients who develop SIRS/sepsis and those who don't.

IL-6 (pg/ml) kinetics in un-symptomatic patients pre- and post-surgery. Comparison between patients who develop SIRS/sepsis and those who don't.

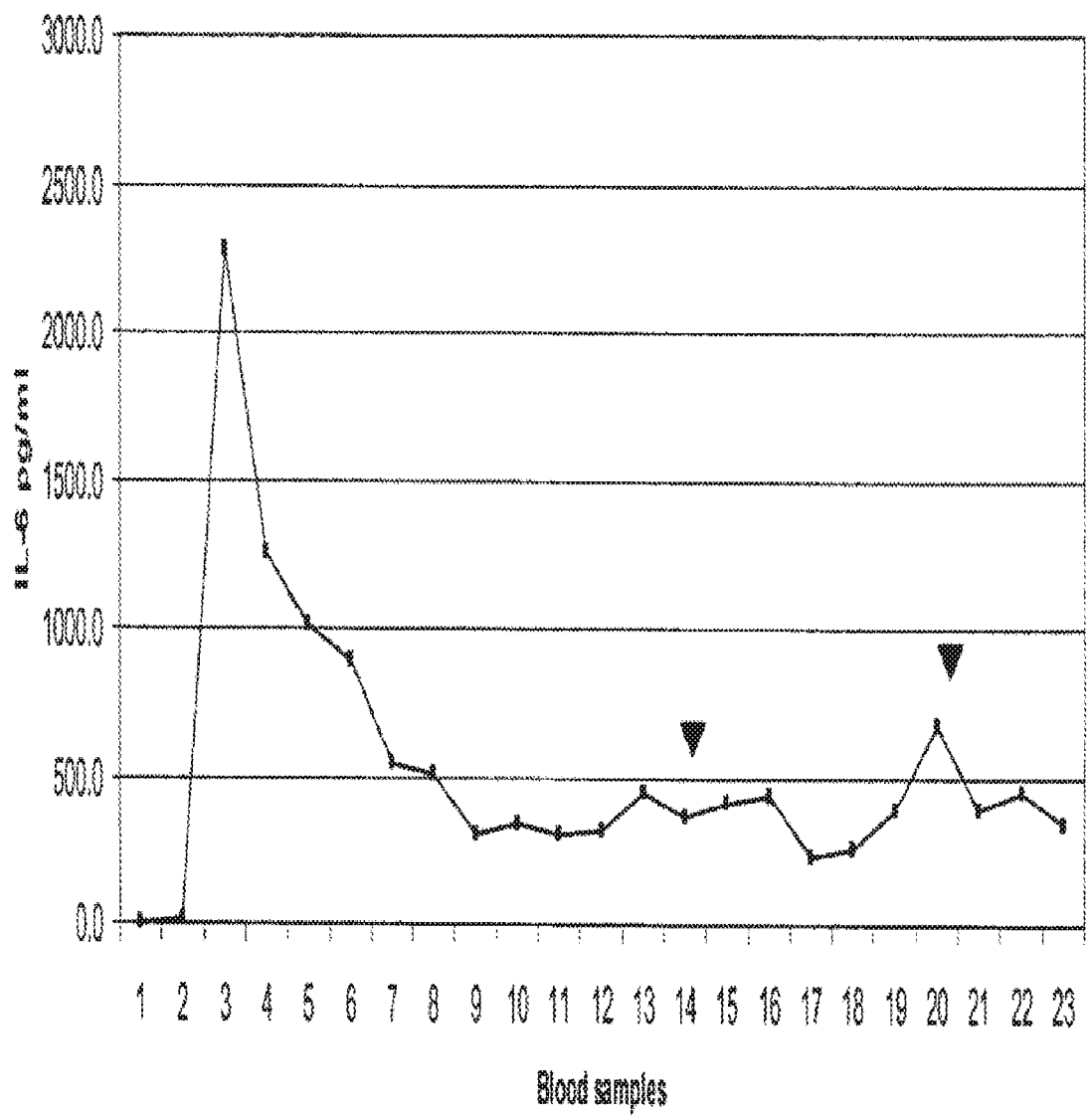

SIRS patient 3

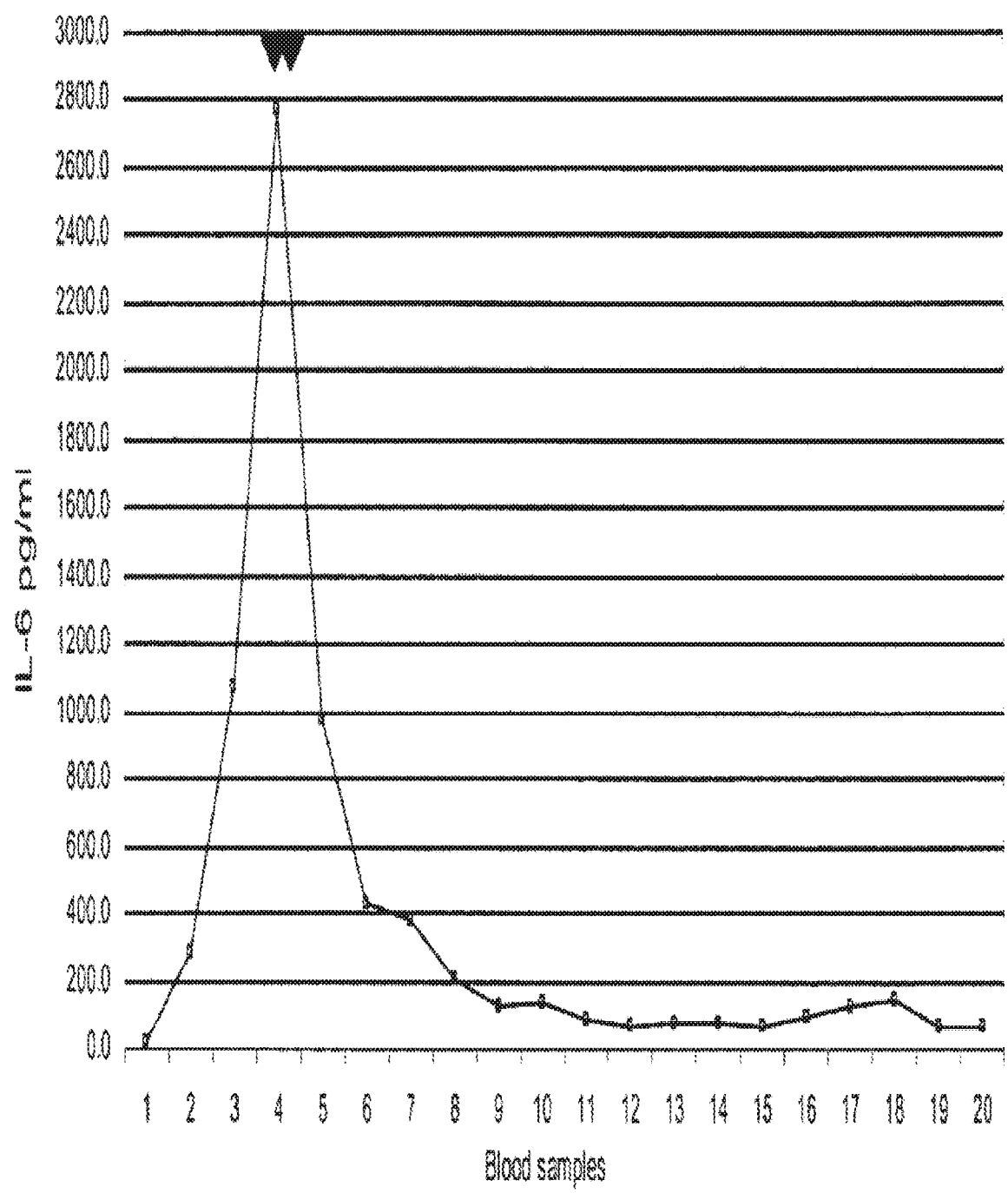

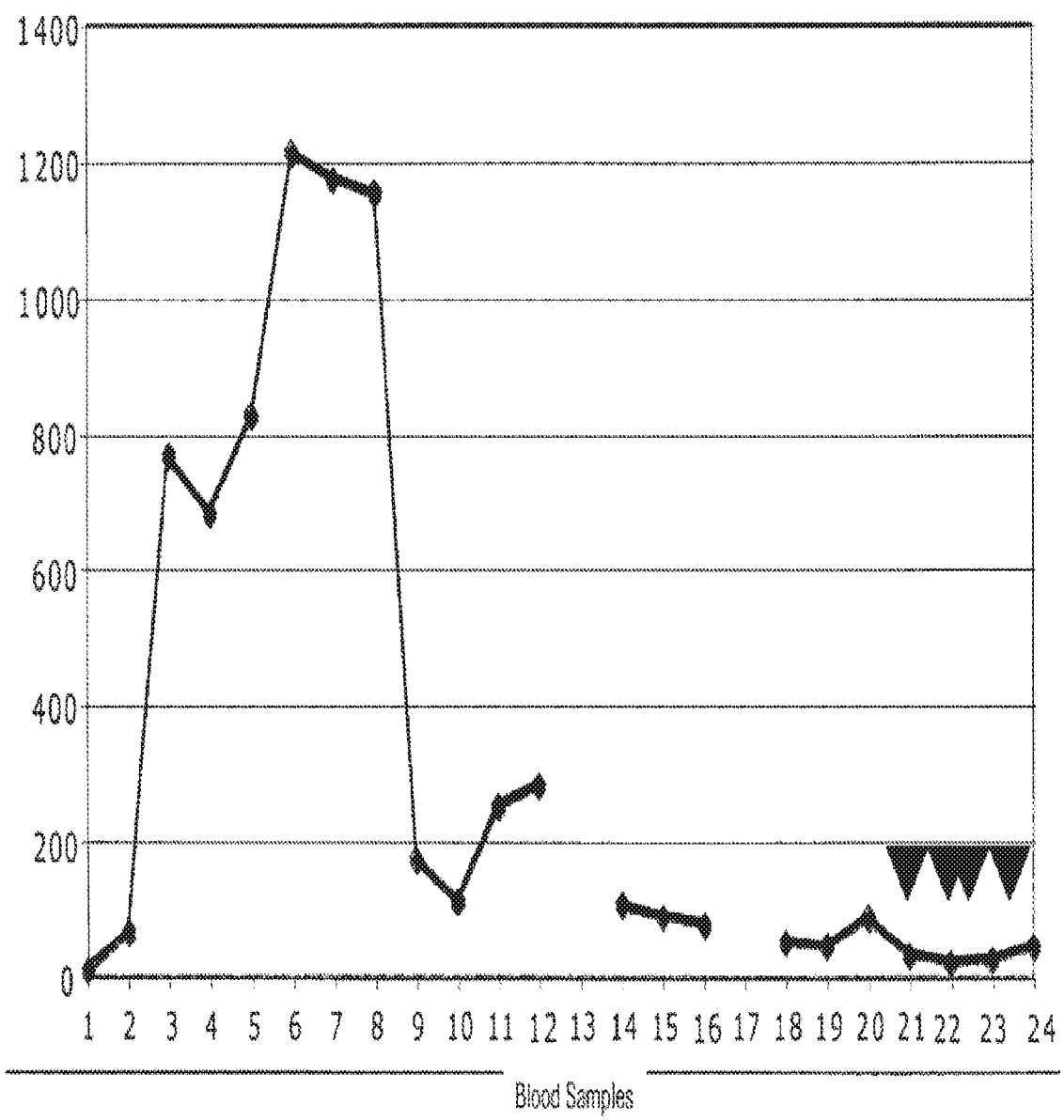

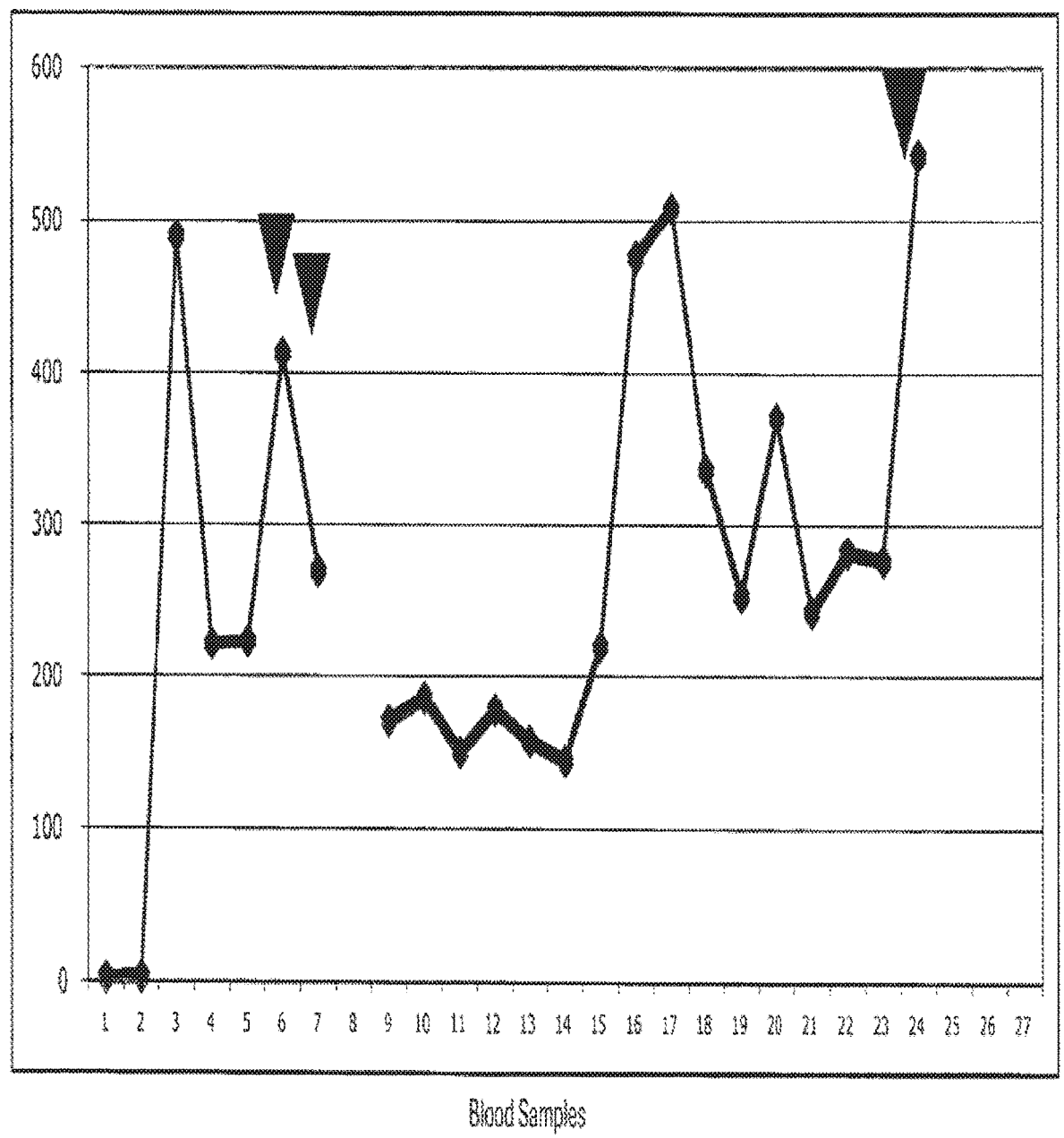

SIRS Patient 7

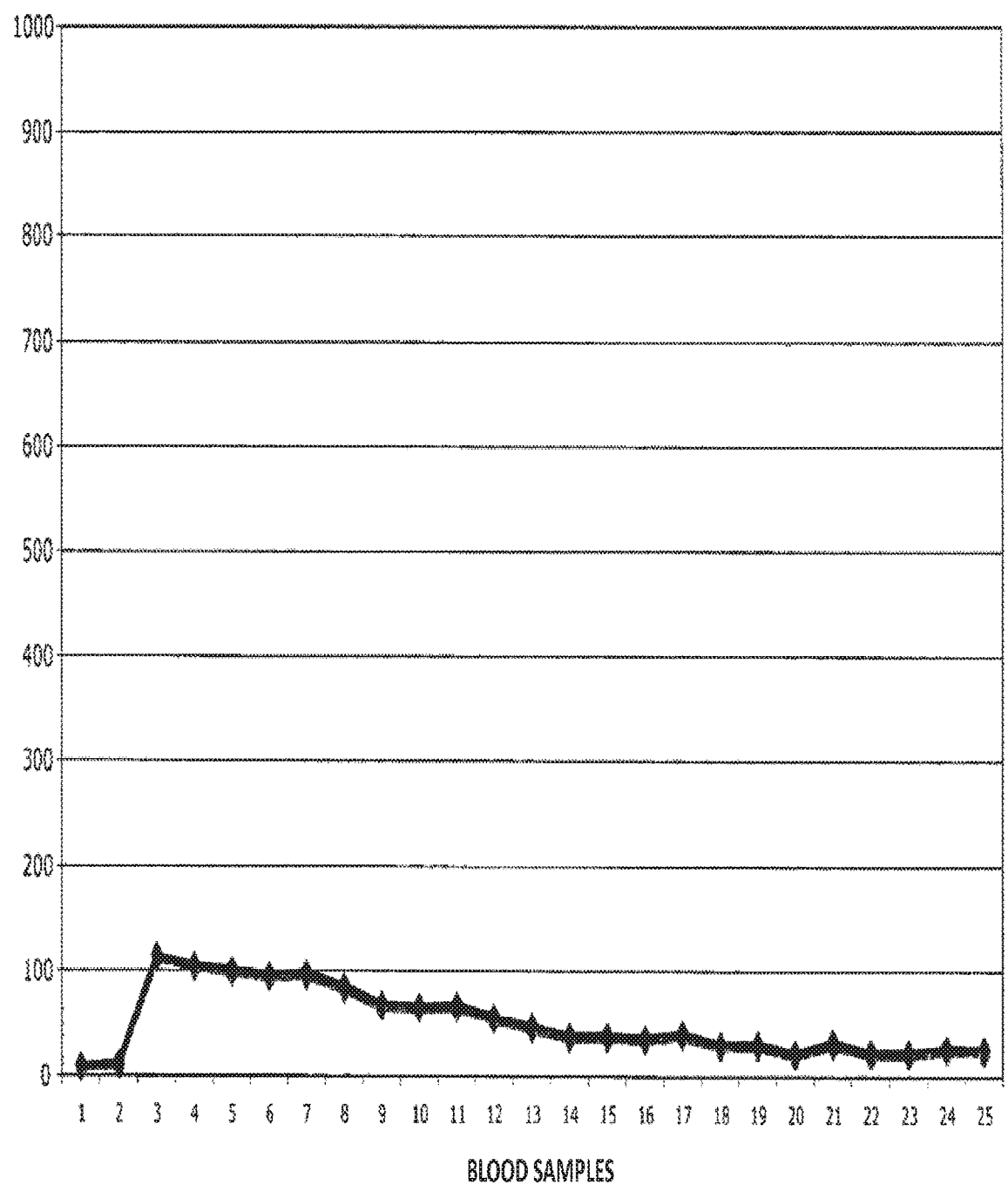

CRP kinetics in unsymptomatic patients pre- and post-surgery. Comparison between patients who develop SIRS/sepsis and those who don't.

CRP kinetics in un-symptomatic patients pre- and post-surgery. Comparison between patients who develop SIRS/sepsis and those who don't.

CRP kinetics in un-symptomatic patients pre- and post-surgery. Comparison between patients who develop SIRS/sepsis and those who don't.

IL-6 (pg/ml) kinetics in un-symptomatic patients pre- and post-surgery. Comparison between patients who develop SIRS/sepsis and those who don't.

IL-6 DETECTION BASED EARLY DIAGNOSIS AND PREDICTION OF SYSTEMIC INFLAMMATORY RESPONSE SYNDROME AND SEPSIS IN ASYMPTOMATIC PATIENTS

CROSS-REFERENCE TO RELATED APPLICATIONS

This application is a divisional application of U.S. application Ser. No. 13/601,787, filed Aug. 31, 2012, which is a continuation of International Application No. PCT/EP2011/001006, filed Mar. 2, 2011, which claims the benefit of European Patent Application No. 10002190.6, filed Mar. 2, 2010, the disclosures of which are hereby incorporated by reference in their entirety.

INCORPORATION OF SEQUENCE LISTING

The instant application contains a Sequence Listing which has been submitted in ASCII format via EFS-Web and is hereby incorporated by reference in this entirety. Said ASCII copy, created on Nov. 9, 2013, is named SEQUENCE_LISTING_26622US.txt, is two thousand three hundred and thirty-nine bytes in size, and is herein incorporated by reference. This Sequence Listing consists of SEQ ID NO:1.

BACKGROUND OF THE DISCLOSURE

Systemic inflammatory response (SIRS) and sepsis represent a common and devastating syndrome that is increasing in frequency around the world. SIRS and sepsis are among the most frequent causes of death in intensive care patients.

In 1991, the American College of Chest Physicians (ACCP) and the Society of Critical Care Medicine (SCCM) provided a conceptual and practical framework to define the systemic inflammatory response to infection (American College of Chest Physicians/Society of Critical Care Medicine Consensus Conference: definitions for sepsis and organ failure and guidelines for the use of innovative therapies in sepsis. Crit Care Med. 1992 June; 20(6):864-74). Uniform definitions for the various stages of sepsis which could be universally and uniformly applied to patients suffering from these disorders were also provided by the joint ACCP and SCCM Conference. Prior to this time, various terminologies were used interchangeably, leading to much confusion.

At the time point when the clinical signs of SIRS and sepsis appear, the development and aggravation of the SIRS has already begun. However, no current methods exist for diagnosing SIRS and sepsis, or for predicting the risk to suffer from or to develop SIRS and sepsis, prior to the onset of such generally recognized clinical signs and symptoms of SIRS and sepsis (for example, in an asymptomatic patient).

BRIEF SUMMARY OF THE DISCLOSURE

The present disclosure provides early diagnosis and prediction of systemic inflammatory response syndrome (SIRS) or sepsis in asymptomatic patients, such as in patients undergoing a surgical intervention, using IL-6 as a diagnostic and predictive biomarker. Corresponding therapy monitoring and mortality prediction methods, kit of parts are also provided. The diagnostic methods and treatment monitoring methods provided herein allow for a sensitive and early detection of SIRS or sepsis and for predicting the risk to suffer from or develop SIRS and sepsis, before the onset of clinical signs and symptoms of SIRS.

The present disclosure also provides methods and treatments for monitoring method, both of which enable early detection of the risk to suffer from or develop SIRS and sepsis before the onset of clinical symptoms. The instant disclosure also provides a kit and a computer program adapted for carrying out these methods.

According to a first embodiment, it is provided a method for detection or diagnosis of a systemic inflammatory response syndrome (SIRS) or sepsis, or for detection or diagnosis of a risk to develop or suffer from SIRS or sepsis, in an asymptomatic patient, comprising the steps of determining the level of IL-6 or a variant thereof in a sample from the patient, comparing the level of IL-6 or a variant thereof determined in step a) to a reference level and detecting or diagnosing SIRS, or detecting or diagnosing a risk to develop or suffer from SIRS or sepsis. In some such embodiments, the sample may be isolated at least 2 times at short intervals and the steps of determining and comparing are repeated for each sample.

In some embodiments, it is provided a method for detecting the level of IL-6 in an asymptomatic patient for detection or diagnosis of a risk to develop or suffer from SIRS or sepsis, comprising the steps of determining the level of IL-6 or a variant thereof in a sample from the patient and comparing the level of IL-6 or a variant thereof determined in the determining step to a reference level. According to various embodiments, based on the comparison it is detected or diagnosed if the patient is at risk to develop or suffer from SIRS or sepsis. In some embodiments, the sample is isolated at least 2 times at short intervals and the determining and comparing steps are repeated for each sample.

Yet in further embodiments of the instant disclosure, it is also provided a method for detection or diagnosis of a risk to develop or suffer from SIRS or sepsis, in an asymptomatic patient selected from a trauma patient, a patient with burns, a patient undergoing an invasive treatment, a patient undergoing a surgery, comprising the steps of determining the level of IL-6 or a variant thereof in a sample from the patient and comparing the level of IL-6 or a variant thereof determined in the step of determining to a reference level. The method also includes detecting or diagnosing SIRS, or detecting or diagnosing a risk to develop or suffer from SIRS. The sample is isolated at least 2 times at short intervals and the determining and comparing steps are repeated for each sample. In some embodiments, at least one sample is isolated upon admission of the patient and at least one sample is isolated after a treatment has been initiated or terminated.

In some embodiments of the above described embodiments, if the asymptomatic patient will be subjected to a invasive treatment at least one sample is isolated before the surgical intervention or to obtain a baseline IL-6 level, then at least one further sample is isolated and analyzed for IL-6 levels at short intervals after the completion of the invasive treatment.

Additionally, embodiments of the instant disclosure include IL-6 or a means for detecting IL-6 used to detect or diagnose the risk to develop or suffer from SIRS or sepsis, in an asymptomatic patient, wherein the level of IL-6 is determined at least 2 times at short intervals.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIGS. 1a-1f are a graph presenting IL-6 (pg/ml) kinetics in asymptomatic patients pre- and post-surgery showing a comparison between pooled patients who developed SIRS/sepsis and those who did not (having IL-6 levels plotted for baseline 1 (pre-surgery), baseline 2 (during surgery), and post-surgery (day 1, 2, 3 and 4 in which samples were taken at 6 hour intervals) and having Median and the percentiles indicated).

FIG. 2a is a graph presenting the concentration of IL-6 (pg/ml) plotted over time for SIRS patient No. 1 (with the darkened triangle indicating the time point clinical SIRS signs were diagnosed).

FIG. 2d is a graph presenting the concentration of IL-6 (pg/ml) plotted over time for SIRS patient No. 4 (with the darkened triangle indicating the time point clinical SIRS signs were diagnosed).

FIG. 2e is a graph presenting the concentration of IL-6 (pg/ml) plotted over time for SIRS patient No. 5 (with the darkened triangle indicating the time point clinical SIRS signs were diagnosed).

FIG. 2f is a graph presenting the concentration of IL-6 (pg/ml) plotted over time for SIRS patient No. 6 (with the darkened triangle indicating the time point clinical SIRS signs were diagnosed).

FIG. 3 is a graph presenting the median concentration of IL-6 (pg/ml) plotted over time for non-SIRS patients.

Figure 1A:
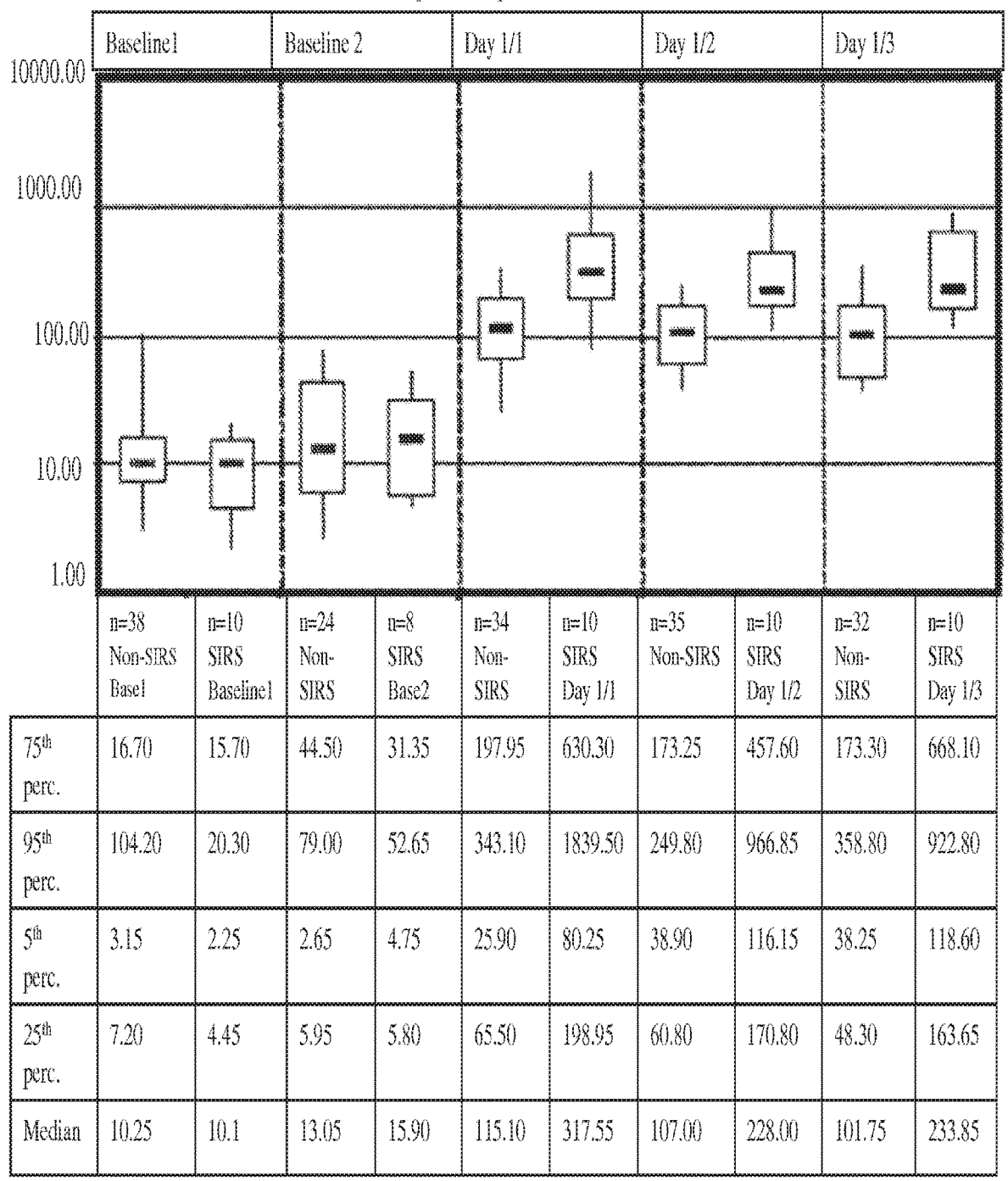

SEQ ID NO.1: is the human 212 amino acid long IL-6 precursor.

SEQ ID NO.1: is the human 212 amino acid long IL-6 precursor set forth at NCBI Assession number NP_000591.

Although the sequence listing represents an embodiment of the present disclosure, the sequence listing is not to be construed as limiting the scope of the disclosure in any manner and may be modified in any manner as consistent with the instant disclosure and as set forth herein.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

SEQ ID NO.1: is the human 212 amino acid long IL-6 precursor.

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

A number of conditions associated with a risk of developing sepsis and severe sepsis have been identified through epidemiological evaluation. These factors include: gender (men); race (black); ethnicity (Hispanic); advanced age; and co-morbidities Diabetes mellitus, malignancy, alcoholism, HIV infection, and treatment with immunosuppressive agents (Hodgin K E, Moss M., The epidemiology of Sepsis. Current Pharm Design, 2008; 14:1833-1839, the disclosure of which is hereby incorporated by reference in its entirety). In addition, an event such as a major surgery, trauma, or burn which results in large area wounds also presents an additional risk. SIRS without infection may also occur in events such as pancreatitis, shock, ischemia, and polytrauma.

IL-6 belongs to a family of gp130 cytokines. All family members share a four-helical protein structure and exert a signal via a receptor complex containing at least one subunit of the signal transducing receptor glycoprotein gp130. IL-6 binds to the IL-6 receptor (IL-6R) first and this IL-6/IL-6R complex binds to gp130 leading to a homodimerization and subsequent activation of the Jak/Stat- and Ras/Map/Akt-signal transduction pathway. There are two different signaling pathways, one in which IL-6 binds to the membrane bound IL-6 receptor which leads to dimerization and activation of the signal transducing protein gp130. This pathway is restricted to cells which express the IL-6 receptor on their surface, which is only the case in some cell populations. However an alternative pathway exists in which IL-6 binds to a naturally occurring soluble IL-6R (sIL-6R) and this IL-6/sIL-6R complex activates gp130. This way, cells lacking the membrane bound IL-6-receptor can respond to IL-6. This second so called trans-signaling pathway also affects cells which express membrane-bound IL-6 receptors (for example, hepatocytes). In this setting an activation of IL-6 trans-signaling can enhance stimulatory effects of IL-6.

IL-6 has shown activity in both B-cells, T-cells, hematopoietic stem cells, hepatocytes and brain cells. Body fluids of patients with local acute infection and serum of patients with gram-negative and gram-positive bacteraemia have been shown to contain elevated levels of biologically active IL-6. Also, IL-6 presence serum during acute infection has been shown (suggesting this cytokine may participate in both local and systemic events for limiting tissue damage).

However, diagnosing SIRS and sepsis, predicting the risk to suffer from or to develop SIRS and sepsis, before the onset of generally recognized clinical signs and symptoms of SIRS and sepsis (for example, in an asymptomatic patient) has not been demonstrated or suggested. The present disclosure provides a surprising and unexpected method and system for a diagnostic method and a treatment monitoring method allowing for a sensitive and early detection of SIRS or sepsis and for predicting the risk to suffer from or develop SIRS and sepsis, before the onset of clinical signs and symptoms of SIRS.

The present disclosure also provides means and methods which solve at least some of the shortcomings of the hitherto known approaches to diagnosing SIRS and sepsis. Moreover, the methods and treatments provided include monitoring methods which allow for an early detection of the risk to suffer from or develop SIRS and sepsis before the onset of clinical symptoms. Further, the present disclosure provides kits and computer programs adapted for carrying out these methods.

The instant disclosure sets forth a method and system which provides the surprising and unexpected result of allowing for a clear identification of asymptomatic patients at risk of suffering from or developing SIRS including sepsis well before the onset of clinical signs or pathological changes of laboratory parameters conventionally used to diagnose SIRS/sepsis (see e.g. Examples). According to the instant disclosure, close-meshed consecutive measurements of IL-6, for example beginning before a treatment (such as a therapy associated with a significant risk of resulting in SIRS or sepsis) such as a major surgery, allows for a clear identification of asymptomatic patients at risk of suffering from or developing SIRS including sepsis well before the onset of clinical signs or pathological changes of laboratory parameters conventionally used to diagnose SIRS/sepsis. The instant disclosure sets forth, for the first time, IL-6 kinetics in asymptomatic patients which can be useful in identifying such patients as developing (or at risk for developing) SIRS. As disclosed herein, a large rise in IL-6 concentration when compared to a baseline level indicates a high risk to develop or suffer from SIRS or sepsis, well ahead of the display of clinical symptoms or signs supporting the diagnosis of SIRS and sepsis. Thus, contrary to what was known before, rather than analyzing the absolute level of IL-6 in the sample, the diagnosis of the risk to suffer from or develop SIRS or sepsis is essentially based on determining the increase of the IL-6 level over time. Furthermore, the early response properties of the method of the present disclosure enables, prior to the appearance of clinical signs and symptoms of SIRS and sepsis, the ability to initiate appropriate treatments at an earlier point in time, when compared to hitherto known method of diagnosing SIRS and sepsis. The instant disclosure further provides methods and systems which enhance the likelihood of a successful therapy to SIRS, or the prevention of SIRS or sepsis, and therefore provides for the improvement of treatments of patients against SIRS or sepsis.

As used herein, the phrase "systemic inflammatory response syndrome (SIRS)" is generally known to the skilled worker. According to the instant disclosure, this phrase encompasses SIRS as defined on the ACCP/SCCM Consensus Conference Definitions (1992/2003) (see e.g. American College of Chest Physicians/Society of Critical Care Medicine Consensus Conference: definitions for sepsis and organ failure and guidelines for the use of innovative therapies in sepsis. Crit Care Med. 1992 June; 20(6):864-74)). A patient is generally considered to suffer from SIRS, if the patient displays at least 2 symptoms of the following:
a) white blood cell count (WBC)>about 12,000/μ/L or <about 4000/μ/L;
b) body temperature>about 38° C. or <about 36° C.;
c) heart rate>about 90 beats/minute;
d) a respiratory rate>about 20 breaths/minute or a partial pressure of $CO_2$ of less than about 32 mm Hg; and
e) more than 10% immature white blood cells among the counted white blood cells.

At the time point when the clinical signs appear, the development and aggravation of the SIRS has already been started.

White blood cell counts may generally be determined by automated counting devices, for example, as known in the art.

With regard to children, the consensus criteria for diagnosing SIRS in a child are disclosed in Goldstein et al. (Pediatr. Crit Care Med 2005, 6(1), 2-8, see in particular Tables 2 and 3, the disclosure of which is hereby incorporated by reference in its entirety). An asymptomatic child patient in the sense of the present disclosure is a patient displaying less than 2, and in some cases less than 1 symptom of those described in Goldstein et al.

As disclosed and described herein, the risk of suffering from or developing SIRS may be diagnosed or detected on the basis of an IL-6 level detected in a sample of a patient which is above the reference level. According to embodiments of the instant disclosure, the detection and diagnosis set forth herein do not require the patient to display at least two of the above SIRS symptoms (a) to (e). As disclosed herein, the risk to suffer from or develop SIRS or sepsis may be diagnosed or detected solely on the basis of a determined IL-6 level which is above the reference level. In some embodiments, the reference value is determined by multiplying an earlier determined IL-6 level (e.g. a baseline IL-6 level) in a given patient by a factor defined elsewhere herein (e.g. a factor of at least about 50, at least about 100, at least about 500, and in some embodiments at least about 1000). According to embodiments of the instant disclosure, IL-6 levels determined in one or more samples isolated from the patient after the earlier sample(s) (which provide the baseline level) was collected, and which comprise IL-6 levels above the reference level are indicative of the patient to be at a high risk to develop or suffer from SIRS. The present disclosure provides that, based on the IL-6 determinations disclosed and taught herein, early detection and diagnosis of the risk to suffer from or develop SIRS is possible, even before the patient displays two or more of the above SIRS symptoms (a) to (e).

As used herein, for "sepsis" the diagnostic criteria mentioned for "SIRS" above applies mutatis mutandis, however, in sepsis, a diagnosed infection is a additional diagnostic parameter generally required. Methods for the detection or diagnosis of an infection are generally known in the field. The present disclosure provides that the risk to suffer from or develop sepsis may now be detected or diagnosed on the basis of only two parameters, i.e. a level of IL-6 above the reference level and a diagnosed infection.

An "infection" in the sense of the present disclosure may be viral, fungal or bacterial infection. According to some embodiments, the infection may be a bacterial infection associated with bacteria selected from *E coli, Staphylococcus aureus, Klebsiella pneumoniae, Streptococci* or *Pseudomonas aeruginosa*. Also, by way of example, the infection may also be an infection by a fungus selected from *Candida albicans, Candida tropicalis* or *Aspergillus fumigatus*, for example.

An infection is diagnosed on the basis of assays and criteria generally known to the physician. For example, the infection may be diagnosed on the basis of a bacterial culture assay, e.g. a culture medium inoculated with a sample from the patient, or based on molecular diagnostic methods. A fungal infection may, for example, be determined based on the generally known test assays such as Septifast.

The term "patient" as used herein relates to animals, including mammals such as but not limited to humans, dogs, cats, horses, and cattle. Humans include male or female, and also includes prenatal, perinatal, postnatal or neonatal children.

As used herein, the expression "asymptomatic patient" encompasses a patient not displaying clinical signs and symptoms generally considered to establish diagnosis of SIRS. For example, the asymptomatic patient in general will display less than 2 symptoms and in some cases, less than 1 symptom of the following:
  a) white blood cell count (WBC)>about 12,000/μ/L or <about 4000/μ/L;
  b) body temperature>about 38° C. or <about 36° C.;
  c) heart rate>about 90 beats/minute;
  d) a respiratory rate>about 20 breaths/minute or a partial pressure of $CO_2$ of less than about 32 mm Hg; and
  e) more than 10% immature white blood cells among the counted white blood cells.

The instant disclosure is also applicable with a asymptomatic patients which include trauma patients, patients with burns, patients undergoing an invasive treatment such as a surgical intervention (including and endoscopic intervention), and patients selected from findings on a CT-scan or PET-CT-scan. The instant disclosure is further applicable with asymptomatic patients having a risk of developing SIRS or sepsis such as a patient meeting at least one of the following criteria:
  genetic disposition for sepsis;
  premature (perinatal, neonatal) or advanced age;
  sex is male;
  race is African American;
  medical co-morbidities including a chronic illness (like diabetes, congestive heart failure), pre-existing organ dysfunction (like cirrhosis or renal failure), physical or mental impairment;
  previous clinical interventions (like major surgery, endotracheal intubation, antibiotics); and
  social, religious or cultural factors.

The aforementioned criteria are described in further detail in Marshall J C ("Predisposition to Sepsis", Anaesthesia, Pain, Intensive Care and Emergency A.P.I.C.E., Springer Verlag, ISBN 88-470-0772-0, the disclosure of which is hereby incorporated by reference in its entirety). These factors may be taken into account when practicing the methods and systems of the present disclosure.

According to some embodiments, asymptomatic patients may exclude a patient where the metabolization of IL-6 is impaired (for example, patients where IL-6 clearance via the splanchnic and kidney organ is impaired as discussed in Garibotta et al., Cytokine, 2007, 37, 51-54, the disclosure of which is hereby incorporated by reference in its entirety).

According to the present disclosure, "interleukin-6 (IL-6)" encompasses IL-6, as it is generally known in the art. For example, IL-6 encompasses interferon-β2, plasmacytoma growth factor, hepatocyte stimulating factor and human B-cell-stimulating factor 2 (BSF2). IL-6, as used herein, may also comprise a protein produced from a single gene encoding a product of 212 amino acids, or in some cases a product of 184 amino acids of the IL-6 peptide which is cleaved at the N-terminus of the 212 amino acid peptide (see Song M, Kellum J A. Interleukin-6. Crit Care Med 2005; 33 (Suppl12): 463-465 and NCBI sequence for the 212 amino acid long IL-6 precursor, accession number NP_000591, the disclosure of which is hereby incorporated by reference in its entirety). IL-6 also encompasses free IL-6 which is not bonded to its receptor IL-6R. Moreover, IL-6 may also encompass IL-6 in the state of the IL-6/IL-6R complex (see Taga T, Kishimoto T. Gp130 and the Interleukin-6 Family of Cytokines. Annu. Rev. Immunol. 1997; 15: 797-819; Drucker C, Gewiese J, Malchow S, Scheller J, Rose-John S. Impact of Interleukin-6 Classic- and Trans-signaling on Liver Damage and Regeneration. J Autimm 2009 in press). IL-6 may also comprise the IL-6 protein which can be bound or which is bound by the monoclonal anti-IL6 antibody M-BE8 (as defined in EP0430193, i.e. an antibody produced by the cell line BE-8, or in KLEIN, B., et al. 1991, Murine anti-interleukin 6 monoclonal antibody therapy for a patient with plasma cell leukemia, Blood 78, 1198-1204) or M-23C7. Also, IL-6 may comprise the IL-6 which can be bound or which is bound by the antibody of Roche's IL-6 assay for use on Elecsys and cobas immunoassay systems (Roche). As used herein, IL-6 also encompasses a variant of the aforementioned IL-6, such as human IL-6. The variant encompasses a protein or peptide substantially similar to the specific reference IL-6 molecule, such as the human IL-6. As used herein, the term substantially similar is well understood by the person skilled in the art.

Some embodiments of the instant disclosure may comprise an IL-6 variant. According to the present disclosure and IL-6 variant may be an isoform or allele which shows at least one amino acid exchange including substitutions, additions and deletions (for example, in some cases up to about 3, up to about 5, up to about 10, up to about 15, and even up to about 25 amino acid exchanges) compared to the amino acid sequence of the specific reference IL-6 molecule. In some embodiments, an IL-6 variant has a sequence identity to the specific reference IL-6 molecule of at least about 80%, at least about 85%, at least about 90%, at least about 95%, at least about 98%, with respect to human IL-6. Such identity, according to some embodiments, is over the entire length of the human IL-6. The degree of identity between two amino acid sequences can be determined by algorithms well known in the art, for example. In general, the degree of identity is determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage can be calculated, for example, by determining the number of positions at which the identical amino acid residue occurs in both sequences to yield the number of matched positions, dividing the number of matched positions by the total number of positions in the window of comparison and multiplying the result by 100 to yield the percentage of sequence identity. Examples of algorithm for optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.). Alignment of sequences of comparison may also be accomplished by visual inspection. Given that two sequences have been identified for comparison, GAP and BESTFIT may be employed to determine their optimal alignment and, thus, the degree of identity. In such embodiments, default values of 5.00 for gap weight and 0.30 for gap weight length may be used.

Variants as referred to above (and herein) may be allelic variants or any other species specific homologs, paralogs, or orthologs. The expression variant also encompasses degradation products, e.g. proteolytic degradation products, which are still recognized by the diagnostic means or by ligands directed against the respective full-length protein or peptide. The term "variants" is also meant to cover splice variants and also relates to a post-translationally modified peptide such as glycosylated peptide. A "variant" is also a peptide which has been modified after collection of the sample, for example by covalent or non-covalent attachment of a label, such as a radioactive or fluorescent label, to the peptide. In some embodiments, the IL-6 variant possesses essentially the same immunological and/or biological properties of the specific reference peptide, which in some cases is human IL-6. Also, according to various embodiments, the IL-6 variant may display at least about 70%, at least about 80%, at least about 90%, at least about 95%, or at least about 98% of the human IL-6 activity. The IL-6 activity according to some embodiments is defined as the IL-6 receptor binding activity (see Taga T, Kishimoto T. Gp130 and the Interleukin-6 Family of Cytokines. Annu. Rev. Immunol. 1997; 15: 797-819; Drucker C, Gewiese J, Malchow S, Scheller J, Rose-John S Impact of Interleukin-6 Classic- and Transsignaling on Liver Damage and Regeneration. J Autimm 2009 in press.). The IL-6 variant, according to some embodiments, displays a human IL-6 receptor binding activity of at least about 80%, at least about 90%, or at least about 95% of human IL-6.

According to a some embodiments of the present disclosure at least one additional marker or parameter indicative of SIRS or sepsis is determined including at least one parameter selected from an inflammation marker like CRP, another interleukin like IL-1 and/or IL-8, procalcitonin, white blood cell count, body temperature, heart rate, respiratory rate, and/or diagnosis of an infection, preferably a bacterial and/or fungus infection.

Moreover, the method of the present disclosure may comprise steps in addition to those explicitly mentioned above. For example, further steps may relate to sample collection, sample pre-treatments or evaluation of the results obtained by the method. The method of the present disclosure may be also used for monitoring, confirmation, subclassification and risk assessment of developing or suffering from SIRS and for therapeutic monitoring the diseases of the present disclosure. It is also envisioned that in some embodiments at least one additional marker or parameter may be determined apart from the two mentioned in step a), such as for the purpose of obtaining additional diagnostic information beyond the detection or diagnosis of SIRS or sepsis. Such additional parameter may for example be the estimated glomerular filtration rate, the level of NGAL or creatinine which allows to additionally diagnose if the patient suffers from an impaired renal clearance.

The method may be carried out manually and/or assisted by automation. For example, steps (a), (b), and/or (c) may in total or in part be assisted by automation, e.g., by a suitable robotic and sensory equipment for the determination in step (a) or a computer-implemented comparison in step (b) and/or (c).

The term "sample" as used herein refers to a sample of a body fluid, to a sample of separated cells, or to a sample from a tissue or an organ. Samples of body fluids can be obtained by well-known techniques and include, but are not limited to, samples of blood, plasma, serum, liquor or urine. In some cases, body fluid samples are obtained by venopuncture, arterial puncture or ventricular puncture. Tissue or organ samples may be obtained from any tissue or organ by, for example, biopsy. Separated cells may be obtained from the body fluids or the tissues or organs by separating techniques such as centrifugation or cell sorting. In some embodiments, cell-, tissue- or organ samples are obtained from those cells, tissues or organs which express or produce the peptides referred to herein.

Further, the methods of the present disclosure may encompass a step of collecting a sample, which optionally may be an invasive step. However, the sample may be collected by way of a minimal invasive step, such as by venopuncture, as well. The minimal invasive collection also encompasses the case where the sample is collected by use of a needle (lancette) which when applied to the skin (for example the skin of a finger) elicits outflow of a small volume of blood which may then be collected for determining the amount of the markers in the sample.

The present disclosure, according to some embodiments, consists of an ex vivo or in vitro method. According to such embodiments, the samples may be isolated at short intervals from a patient. As used herein, "short intervals" encompasses an interval ranging from about 15 minutes to about 12 hours. The samples, according to some embodiments are isolated from the patient for a period of up to about 10 days (although in various embodiments the period may be up to only about 2 or about 3 days). Depending on the condition and development of the condition of the patient the isolation of the samples and IL-6 detection may be further prolonged, for example, if the patient develops SIRS or sepsis the sampling may be extended until the SIRS or sepsis therapy has been successfully completed or even a few days beyond that point in time. According to the instant disclosure the samples are taken at least once, and in some cases at least about twice before a treatment is carried out, and then at least once or at least about twice after the treatment. For example, prior to the treatment being carried out, one or two IL-6 levels may be taken. Following the treatment a number of samples may be taken at regular intervals such as 3-6 hours over a period of about 3 to 10 days, where IL-6 (and in some embodiments also the clinical status) of the patient is determined.

The phrase "detecting and diagnosing SIRS" as used herein means assessing, identifying, evaluating, or classifying if an asymptomatic patient suffers from SIRS, preferably from sepsis.

The phrase "detecting and diagnosing a risk to develop or suffer from SIRS" is meant to encompass the prediction of the risk in an asymptomatic patient to develop or to suffer from SIRS, including sepsis, within a defined time window (predictive window) in the future. The predictive window is an interval in which the subject will develop a SIRS or optionally will die according to the predicted probability. In some cases, the predictive window is an interval of up to about 20 days, but may be up to about 10 days or less such as about 7 days, about 5 days, about 4 days, about 3 days, or about 2 days, (i) after the method of the present disclosure has been carried out or (ii) after the first sample was obtained in which the detected IL-6 level was above the reference level or (iii) after admittance of the patient or (iv) after the first baseline level for IL-6 has been obtained/isolated or (v) after the treatment (e.g., the invasive treatment) has been initiated or terminated, or (vi) after the first post-treatment sample has been isolated for determination of the IL-6 level.

Patients identified as being at risk of developing or suffering from SIRS, according to the instant disclosure, may possess a high probability of developing or suffering from SIRS. In general, the high probability will be at least about 30% or more (for example, at least about 40%, at least about 50%, at least about 60%, at least about 70%, at least about 80%, at least about 90%, at least about 95%). Optionally, a high probability of developing or suffering from SIRS or sepsis, encompasses a probability of 100%, i.e. the patient will develop or does suffer from SIRS or sepsis.

Alternatively, the patient may have a low probability of suffering from or developing SIRS or sepsis. For example, the low probability may be up to about or less than about 30%, or up to about 20%, up to about 10%, or up to about 5%. Optionally, a low probability of developing or suffering from SIRS or sepsis, encompasses a probability of 0%, i.e. the patient will not develop or does not suffer from SIRS or sepsis.

Methods for the determination of the % risk of suffering from or developing SIRS or sepsis are generally known. By way of example, the % risk prediction may be carried out within the predictive window mentioned above.

According to the instant disclosure, the extent of the risk to develop or suffer from SIRS or sepsis may correlate with the extent the detected IL-6 level is above the reference value. Likewise, the risk of developing or suffering from SIRS or sepsis may be low in cases where the detected IL-6 level is lower than the reference level. Further, at least according to some embodiments, the risk of developing or suffering from SIRS or sepsis is high in cases where the detected IL-6 level is equal to or above the reference value.

As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined by the person skilled in the art using any of various well known statistic evaluation tools, including by not limited to, a determination of confidence intervals, p-value determination, Student's t-test, Mann-Whitney test, etc. Details of some tools may be found in Dowdy and Wearden, Statistics for Research, John Wiley & Sons, New York 1983. In some instances, confidence intervals are at least 90%, at least 95%, at least 97%, at least 98% or at least 99%. The p-values are, in some embodiments, are 0.1, 0.05, 0.01, 0.005, or 0.0001. Also, the probability encompassed by the present disclosure allows that the prediction will be correct for at least 60%, at least 70%, at least 80%, or at least 90% of the subjects of a given cohort.

Determining the level of IL-6 or a variant thereof, or of any other proteinaceous biomarker according to the disclosure, relates to measuring the amount or concentration, including semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal, sometimes referred to herein as intensity signal, may be obtained by measuring an intensity value of a specific physical or chemical property of the peptide or polypeptide, for example. Indirect measuring includes measuring of a signal obtained from a secondary component (i.e. a component not being the peptide or polypeptide itself) or a biological read out system such as measurable cellular responses, ligands, labels, or enzymatic reaction products.

In accordance with the present disclosure, determining the amount of an IL-6 peptide or polypeptide can be achieved by all known means for determining the amount of a peptide in a sample. Said means comprise immunoassay devices and methods which may utilize labeled molecules in various sandwich, competition, or other assay formats. Said assays generally develop a signal which is indicative for the presence or absence of the peptide or polypeptide. Moreover, in some embodiments, the signal strength may be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Roche's Elecsys™ analyzers), CBA (an enzymatic Cobalt Binding Assay, available for example on Roche-Hitachi™ analyzers), and latex agglutination assays (available for example on Roche-Hitachi™ analyzers), homogenous and heterogeneous immune assays, competitive and non-competitive immune assays.

According to various embodiments, determining the amount of an IL-6 peptide or polypeptide comprises the steps of (a) contacting a cell capable of eliciting a cellular response, the intensity of which is indicative of the amount of the peptide or polypeptide with the said peptide or polypeptide, for an adequate period of time, and (b) measuring the cellular response. For measuring cellular responses, the sample or processed sample is, in some embodiments, added to a cell culture and an internal or external cellular response is measured. The cellular response may include the measurable expression of a reporter gene or the secretion of a substance such as a peptide, polypeptide, or a small molecule. The expression or substance may generate an intensity signal which correlates to the amount of the peptide or polypeptide.

Also according to embodiments of the instant disclosure, determining the amount of a IL-6 peptide or polypeptide comprises the step of measuring a specific intensity signal obtainable from the peptide or polypeptide in the sample, for example in a sample selected from blood, serum, plasma or liquor. As described above, such a signal may be the signal intensity observed at an m/z variable specific for the peptide or polypeptide observed in mass spectra or a NMR spectrum specific for the peptide or polypeptide.

Determining the amount of a IL-6 peptide or polypeptide may also comprise the steps of (a) contacting the peptide with a specific ligand, (b) (optionally) removing non-bound ligand, (c) measuring the amount of bound ligand. The bound ligand will generate an intensity signal. Binding according to the present disclosure includes both covalent and non-covalent binding.

A ligand according to the present disclosure can be any compound, e.g., a peptide, polypeptide, nucleic acid, or small molecule, binding to the peptide or polypeptide described herein. Exemplary ligands include antibodies, nucleic acids, peptides or polypeptides such as receptors or binding partners for the peptide or polypeptide and fragments thereof comprising the binding domains for the IL-6 peptides, and aptamers, e.g. nucleic acid or peptide aptamers. Methods of preparing such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display.

Means for the detection of IL-6 are generally known in the art and preferably include anti-IL-6 antibodies, including polyclonal and monoclonal antibodies, as well as fragments thereof, such as Fv, Fab and F(ab)2 fragments that are capable of binding IL-6 antigen or hapten. The means for the detection of IL-6 of the present disclosure also include single chain antibodies, chimeric, humanized hybrid antibodies wherein amino acid sequences of a non-human donor antibody exhibiting a desired antigen-specificity are combined with sequences of a human acceptor antibody. Also included is an anti-IL-6 antibody from a mammalian species, such as an antibody selected from human, rat, mouse, goat, sheep, cattle, and camel. In some embodiments the anti-IL-6 antibody is the M-BE8 or M-23C7 anti-IL-6 antibody described above or an antibody binding to the IL-6 epitope recognized by the M-BE8 and/or M-23C7 antibody. The donor sequences will usually include at least the antigen-binding amino acid residues of the donor but may comprise other structurally and/or functionally relevant amino acid residues of the donor antibody as well. Such hybrids can be prepared by several methods well known in the art. According to embodiments of the instant disclosure, the ligand or agent binds specifically to the IL-6 peptide or polypeptide. Specific binding according to the present disclosure means that the ligand or agent should not bind substantially to ("cross-react" with) another peptide, polypeptide or substance present in the sample to be analyzed. For example, the specifically bound IL-6 peptide or polypeptide should be bound with at least 3 times higher affinity than any other relevant peptide or polypeptide. In some embodiments of the instant disclosure, the specifically bound IL-6 peptide or polypeptide may bind with at least at least 10 times higher or even at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Embodiments of the instant disclosure include said method being semi-quantitative or quantitative. Suitable methods are described in the following.

First, binding of a ligand may be measured directly, e.g. by NMR or surface plasmon resonance. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, in some embodiments the amount of substrate is saturating. The substrate may also be labeled with a detectable label prior to the reaction. According to embodiments of the instant disclosure, the sample is contacted with the substrate for an adequate period of time. An adequate period of time refers to the time necessary for a detectable (and in some cases measurable) amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should, in general, specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and/or a streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager. Suitable measurement methods according the present disclosure also include, for example, precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

According to embodiments of the present disclosure, the amount of IL-6 is determined by mass spectrometry method, for example by isotope-dilution micro-HPLC-tandem mass spectrometry method, for example by a method as described in the Examples and in Kobold U et al. (Clin Chem 2008; 54: 1584-6), hereby incorporated by reference in its entirety.

The amount of an IL-6 peptide or polypeptide may also be determined as follows: (a) contacting a solid support comprising a ligand for the peptide or polypeptide as specified above with a sample comprising the peptide or polypeptide and (b) measuring the amount peptide or polypeptide which is bound to the support. The ligand, may be chosen from the group consisting of nucleic acids, peptides, polypeptides, antibodies and aptamers, and may be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

The term "about" as used herein encompasses a range of + and −20% relative to the specific value, amount, concentration, level, etc, e.g. indication of a value of "about 100" is meant to encompass a value of a numerical range of 100+/−20%, i.e. a value range from 80 to 120. For example, the term "about" encompasses a range of + and −10% relative to the specific value, amount, concentration, level, etc., and in some embodiments will encompass a range of + and −5% relative to the specific value, amount, concentration, level, etc.

The term "comparing" as used herein encompasses comparing the level of the IL-6 peptide or polypeptide comprised by the sample to be analyzed with a level of a suitable reference source specified elsewhere in this description. It is to be understood that comparing as used herein refers to a comparison of corresponding parameters or values, e.g., an absolute amount is compared to an absolute reference level while a concentration is compared to a reference concentration or an intensity signal obtained from a test sample is compared to the same type of intensity signal of a reference sample. The comparison referred to in step (b) of the method of the present disclosure may be carried out manually or computer assisted. For a computer assisted comparison, the value of the determined level may be compared to values corresponding to suitable references which are stored in a database by a computer program. The computer program may further evaluate the result of the comparison, i.e. automatically provide the desired assessment in a suitable output format. Based on the comparison of the level determined in step a) and the reference level, the diagnosis of SIRS in a patient is determined. Therefore, the reference level is to be chosen so that either a difference or a similarity in the compared levels allows allocation of subjects in to SIRS or not suffering from SIRS.

Accordingly, the term "reference level", refers to an amount, concentration or value which defines a cut-off. An amount, concentration or value of the parameter above the cut-off results in a different diagnosis when compared to patients displaying a determined amount, level or value of the parameter below the cut-off. Thus, by comparing the actually determined amount, concentration or value of the parameters IL-6, to the respective cut-offs it is possible to diagnose or detect the risk in patients to develop or suffer from SIRS or sepsis.

Of course, the reference level applicable for an individual subject may vary depending on various physiological parameters such as age, gender, subpopulation, alcohol intake, recent infections as well as on the means used for the determination of the polypeptide or peptide referred to herein. A suitable reference level may be determined by the method of the present disclosure from a reference sample to be analyzed together, i.e. simultaneously or subsequently, with the test sample. The reference levels of the present disclosure were confirmed in the Examples.

As will be understood by those skilled in the art, such a diagnostic assessment is usually not intended to be correct for all (i.e. 100%) of the patients to be identified. The term, however, as used herein refers to a diagnostic assessment that is correct such that a statistically significant portion of patients can be identified (e.g. a cohort in a cohort study). Statistically significance, as used herein, can be determined as known in the art using various well known statistic evaluation tools, for example determination of confidence intervals, p-value determination, Student's t-test, Mann-Whitney test etc. Details are found in Dowdy and Wearden, Statistics for Research, John Wiley & Sons, New York 1983. Exemplary confidence within the instant disclosure include intervals that are at least 90%, at least 95%, at least 97%, at least 98% and/or at least 99%. The p-values are, for example, 0.1, 0.05, 0.01, 0.005, and/or 0.0001. In exemplary embodiments of the instant disclosure, at least 60%, at least 70%, at least 80% or at least 90% of the patients of a population can be properly identified by the method of the present disclosure.

In general, for determining the respective levels allowing to establish the desired diagnosis in accordance with the respective embodiment of the present disclosure, ("threshold", "reference level"), the amount(s)/level(s) or amount ratios of the respective peptide or peptides are determined in appropriate patient groups. As stated before, the reference value is may be determined by multiplying an earlier determined IL-6 level (e.g. a baseline IL-6 level) in a given patient, for example in the subject patient, by a factor defined elsewhere herein (e.g. a factor of at least about 50 or at least about 100, or at least about 500 or at least about 1000). In some exemplary embodiments, based on retrospective clinical studies, like the one described in the Examples, where the outcome (no SIRS vs. SIRS vs. sepsis) is analyzed and compared to the changes of the level of IL-6 in patients over time, it is easily possible to statistically verify which "factors" are to be multiplied with a subject patient's baseline IL-6 level in order to establish a reference value which is associated with a specific risk probability of developing or suffering from SIRS or sepsis.

The reference level may also be calculated by multiplying the IL-6 baseline level, by a factor of at least about 50, and in some embodiments by a factor of at least about 100, a factor of at least about 500, or even a factor of at least about 1000. For example, if the asymptomatic patient presenting to the physician or the hospital with a baseline IL-6 level of 10 pg/ml, the calculated reference level may be (according to some embodiments) 500 pg/ml (e.g., a 50-fold increase), 1 ng/ml (e.g., a 100-fold increase), 5 ng/ml (a 500-fold increase), or even 10 ng (a 1000-fold increase). In such a patient, a level of IL-6 detected after subjecting the patient to a treatment (for example, a severe surgery or other invasive procedure) above the indicated reference levels indicates that the patient is at high risk to develop or suffer from SIRS.

As used herein, the "baseline level" encompasses at least one IL-6 level obtained (i) when the patient presents to the physician, the emergency unit, the hospital, the intensive care unit, the surgeon or the anaesthesiologist, (ii) before the therapy is initiated, e.g. before surgery, (iii) during the therapy, e.g. during surgery, and/or (iv) after the treatment has been completed, e.g. after the surgery has been completed. Also encompassed by the term is a baseline level which is determined after subjecting the patient to (e.g. an invasive) a treatment, or example within about 24 hours, (in some cases within about 15, about 12 hours, or about 6 hours after treatment). Alternatively, the baseline level is calculated by determining the median or average IL-6 level among the samples taken up to, but not including, a sample where the IL-6 level increased by more than about 20-fold, by more than about 30-fold, by more than about 50-fold, by more than about 50-fold, by more than about 100-fold, or by more than about 500-fold, relative to said median or average IL-6 level.

The diagnosis and detection of the risk of suffering from or developing SIRS or sepsis can be carried out by determining the respective parameters, preferably by measuring the level of IL-6, using validated analytical methods. The results which are obtained are collected and analyzed by statistical methods known to the person skilled in the art.

Optionally, the reference values are established in accordance with the desired probability of suffering from or being at risk to suffer or develop the disease. For example, it may be useful to choose the median factor to be multiplied with the baseline level from the 60th, 70th, 80th, 90th, 95th or even the 99th percentile of the healthy and/or non-healthy patient collective, in order to establish the reference level(s).

A reference level serving as a threshold may be derived from the upper limit of normal (ULN), i.e. the upper limit of the physiological amount to be found in a population. The ULN for a given population of subjects can be determined by various well known techniques. A suitable technique may be to determine the median of the population for the peptide or polypeptide amounts to be determined in the method of the present disclosure.

A reference level of a diagnostic marker can be established and confirmed, and the level of the marker in a patient sample can simply be compared to the reference level. The sensitivity and specificity of a diagnostic and/or prognostic test depends on more than just the analytical "quality" of the test-they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular parameter of the disclosure, a distribution of marker levels for subjects with and without a disease will likely overlap. Under such conditions, a test does not absolutely distinguish normal from disease with 100% accuracy, and the area of overlap indicates where the test cannot distinguish normal from disease or high risk from low risk to suffer from or develop the disease. A threshold (cut-off, reference level) is selected, above which (or below which, depending on how a marker changes with the disease) the test is considered to be abnormal and below which the test is considered to be normal. The area under the ROC curve is a measure of the probability that the perceived measurement will allow correct identification or prediction of the risk of onset or development of a condition. ROC curves can be used even when test results do not necessarily give an accurate number. As long as one can rank results, one can create an ROC curve. For example, results of a test on "disease" samples might be ranked according to degree of the disease (say 1=low, 2=normal, and 3=high) or probability of suffering from or developing the disease (say 1=low, 2=normal, and 3=high). This ranking can be correlated to results in the "normal" population, and a ROC curve created. These methods are well known in the art, for example as discussed in Hanley et al, Radiology 1982; 143: 29-36, the disclosure of which is hereby incorporated by reference in its entirety.

In certain embodiments, markers and/or marker panels are selected to exhibit at least about 70% sensitivity, and in some cases at least about 80% sensitivity, at least about 85% sensitivity, at least about 90% sensitivity, and even at least about 95% sensitivity, combined with at least about 70% specificity, but in some cases as high as at least about 80% specificity, at least about 85% specificity, at least about 90% specificity, and even at least about 95% specificity. In particular embodiments, both the sensitivity and specificity are at least about 75%, or at least about 80%, or even at least about 85%, about 90%, and even at least about 95%.

In other embodiments, a positive likelihood ratio, negative likelihood ratio, or odds ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain embodiments, markers and/or marker panels are selected to exhibit a positive or negative likelihood ratio of at least about 1.5 or more or about 0.67 or less, in some cases at least about 2 or more or about 0.5 or less, and in still others at least about 5 or more or about 0.2 or less, and in even others at least about 10 or more or about 0.1 or less, and in others at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain embodiments, markers and/or marker panels may be selected to exhibit an odds ratio of at least about 2 or more or about 0.5 or less, at least about 3 or more or about 0.33 or less, at least about 4 or more or about 0.25 or less, at least about 5 or more or about 0.2 or less, and even at least about 10 or more or about 0.1 or less. The term "about" in this context refers to +/−5% of a given measurement.

Panels may comprise at least one additional marker; both specific markers of a disease (e.g., markers that are increased or decreased in bacterial infection, but not in other disease states) and/or non-specific markers (e.g., markers that are increased or decreased due to inflammation, regardless of the cause; markers that are increased or decreased due to changes in hemostasis, regardless of the cause, etc.). While certain markers may not be individually definitive in the methods described herein, a particular "fingerprint" pattern of changes may, in effect, act as a specific indicator of disease state. As discussed above, that pattern of changes may be obtained from a single sample, or may optionally consider temporal changes in one or more members of the panel (or temporal changes in a panel response value).

In some embodiments of the methods of the present disclosure,
  i) a level of IL-6 or a variant thereof determined in step a) at or above to the reference level is indicative of the patient to be at a high risk to suffering or developing SIRS; and
  ii) a level of IL-6 or a variant thereof determined in step a) below the reference level is indicative of the patient to be at a low risk to suffering or developing SIRS.

It has been observed that the IL-6 concentration differs significantly among asymptomatic patients. For example, the following factors contribute to this inter-individual differences: recent alcohol consumption, physical exercise, stress, recent history of infections, injury and in acute hyperglycaemia. Accordingly, in some embodiments of the method of the present disclosure, the IL-6 reference level is determined on a patient-by-patient basis.

Patients displaying IL-6 levels above the reference level may also be closely monitored for the onset of clinical signs and symptoms of SIRS or sepsis. The patients may be subjected to monitoring of the following parameters: IL-6 levels, white blood cell count (WBC) and determination of immature leucocyte forms, body temperature, heart-rate, respiratory rate, collection of microbiological specimens from drainages, serum, tracheobronchial secretions and urine and daily chest roentgenogram. Control endoscopies and radiological workup by ultrasound and CT-scan may also be warranted.

The patients may also be treated as follows: initiation of broad spectrum antibiotic treatment, antifungal treatment. In case of doubt, redo surgery shall be scheduled liberally.

In another aspect of the present disclosure it is provided a method of monitoring an asymptomatic patient the risk to develop or suffer from SIRS or sepsis, comprising the steps of:
  a) determining the level of IL-6 or a variant thereof in a sample from the patient;
  b) comparing the level of IL-6 or a variant thereof determined in step a) to a reference level; and
  c) recommending, deciding on, initiating, continuing, modulating or discontinuing the SIRS or sepsis therapy for the patient based on comparison in step b).

Diagnostic and therapeutic consequences of the above monitoring include: Microbiological specimens from serum, drainages, tracheobronchial secretions, and urine, endoscopic controls, radiological imaging procedures as are ultrasound, chest roentgenograms and CT-scans, initiation of broad spectrum antibiotic treatment or change of pre-existent antibiotic treatment to a more efficient one, antifungal treatment. In case of doubt, redo surgery shall be scheduled liberally.

In case the level of IL-6 or a variant thereof is higher than the reference level, the sample or an additionally collected sample is subjected to an assay to identify the infectious organism, e.g. the bacteria, fungus, etc., contained in the sample. Such assays are generally known in the field and are relevant to the diagnosis of sepsis.

In another aspect of the present disclosure it is provided a method of predicting the risk of mortality in an asymptomatic patient, comprising the steps of
  a) determining the level of IL-6 or a variant thereof in a sample from the patient;
  b) comparing the level of IL-6 or a variant thereof determined in step a) to a reference level;
  c) predicting the risk of mortality for the patient based on comparison in step b).

Unless specified differently, the definitions and embodiments described with respect to the method for detection or diagnosis of a risk to suffer from or develop SIRS, above, also apply mutatis mutandis to the present aspect of the disclosure.

According to yet another aspect of the disclosure it is provided a device adapted for detection or diagnosis of a risk to suffer from or develop SIRS, according to a method described above, comprising:
  a) a first analyzing unit comprising a detection means for IL-6 or a variant thereof, wherein the analyzing unit is adapted for determining the level of the IL-6 detected by the detection means;
  b) an evaluation unit comprising a computer comprising tangibly embedded a computer program code for carrying out the comparison of the determined amount obtained from the first analyzing unit with a suitable data base comprising a corresponding reference level as specified above; wherein the first analyzing unit and the evaluation units are operatively linked to each other.

In some embodiments, the device further comprises means for outputting the required diagnosis and treatment and/or prevention on the basis of the diagnosis or risk prediction of the patient to suffer from or develop SIRS or sepsis. In some embodiments, the device further comprises means for outputting the progress and/or response to a treatment and/or therapy of SIRS or sepsis.

According to yet another aspect of the disclosure it is provided a kit adapted for carrying out the method describe above, comprising:
  means for determining the level of IL-6 or a variant thereof;
  means for comparing the determined level of IL-6 or a variant thereof with reference level; and
  instructions for carrying out the method.

The term "kit" as used herein refers to a collection of the aforementioned compounds, means or reagents of the present disclosure which may or may not be packaged together. The components of the kit may be comprised by separate vials (i.e. as a kit of separate parts) or provided in a single vial. Moreover, it is to be understood that the kit of the present disclosure is to be used for practising the methods referred to herein above. According to some embodiments, all components are provided in a ready-to-use manner for practising the methods referred to above. Further, the kit may contain instructions for carrying out the said methods. The instructions can be provided by a user's manual in paper or electronic form for example. For example, the manual may comprise instructions for interpreting the results obtained when carrying out the aforementioned methods using the kit of the present disclosure.

According to yet another aspect of the disclosure it is provided a computer program comprising computer program code which is suitable for carrying out a method of the disclosure when the computer program is run on a computer. In another aspect of the disclosure it is provided a computer readable medium with a computer program of the disclosure stored thereon. In yet another aspect of the disclosure it is provided a computer program product with a computer program of the disclosure stored thereon. For example, the computer program further comprises means for outputting the required prevention and/or therapy on the basis of the diagnosed disease, the means being stored on a computer readable medium.

Unless specified differently, the definitions and preferred embodiments described with respect to the method detection or diagnosis of a systemic inflammatory response syndrome (SIRS), or for detection or diagnosis of a risk to suffer from or develop SIRS, above, also apply to the present aspect of the disclosure.

In another aspect of the disclosure it is provided a kit adapted for carrying out the method of the present disclosure, comprising:
  i) means for determining the level of IL-6 or a variant thereof;
  ii) means for comparing the determined level of IL-6 or a variant thereof with reference levels; and optionally
  iii) instructions for carrying out the method.

In another aspect of the disclosure, it is provided a method for detection or diagnosis of a systemic inflammatory response syndrome (SIRS) or sepsis, or for detection or diagnosis of a risk to suffer from or develop SIRS, in an asymptomatic patient, comprising the steps of:
  a) determining the level of CRP in a sample from the patient;
  b) comparing the level of CRP determined in step a) to a reference level; and [0140] c) detecting or diagnosing SIRS, or detecting or diagnosing a risk to develop SIRS;
  wherein the sample is isolated at least 2 times at short intervals and steps a) and b) are repeated for each sample.

In another aspect of the present disclosure it is provided a method for detection or diagnosis of the risk to develop or suffer from a systemic inflammatory response syndrome (SIRS) or sepsis, in an asymptomatic patient, comprising the steps of:
  a) determining the level of procalcitonin in a sample from the patient;
  b) comparing the level of procalcitonin determined in step a) to a reference level; and
  c) detecting or diagnosing the risk to develop or suffer from a systemic inflammatory response syndrome (SIRS) or sepsis;
  wherein a sample is isolated at least 2 times at short intervals and steps a) and b) are repeated for each sample.

In another aspect of the disclosure, it is provided an antibody selected from an anti-IL-2 antibody, an anti-IL-3 antibody, an anti-IL-4 antibody, an anti-IL-5 antibody, and an anti-IL-6 antibody.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for detection or diagnosis of the risk to develop or suffer from a systemic inflammatory response syndrome (SIRS) or sepsis, in an asymptomatic patient, comprising the steps of:
  a) determining the level of IL-6 or a variant thereof in a sample from the patient;
  b) comparing the level of IL-6 or a variant thereof determined in step a) to a reference level;
  c) detecting or diagnosing the risk to develop or suffer from a systemic inflammatory response syndrome (SIRS) or sepsis,
  wherein a sample is isolated at least 2 times at short intervals ranging from about 15 minutes to about 12 hours and steps a) and b) are repeated for each sample.

2. The method of 1, wherein the asymptomatic patient is a patient who displays less than 2, preferably less than 1 symptom of the following a) to d), preferably of the following a) to e):
  a) white blood cell count of more than about 12,000/µ/L or less than about 4000/µ/L,
  b) a body temperature of more than about 38° C. or less than about 36° C.,
  c) a heart rate of more than about 90 beats/minute or a partial pressure of $CO_2$ of less than about 32 mm Hg, and
  d) a respiratory rate of more than about 20 breaths/minute,
  e) more than about 10% immature white blood cells among the counted white blood cells, optionally the patient does not display a diagnosed infection.

3. The method of 1 or 2, wherein the short interval ranges from about 1 to 6 hours, preferably from about 1 hour to about 3 hours.

4. The method according to any one of 1 to 3, wherein
  i) a level of IL-6 or a variant thereof determined in step a) above to the reference level is indicative of the patient to be at high risk of suffering or developing SIRS or sepsis; and
  ii) a level of IL-6 or a variant thereof determined in step a) below the reference level is indicative of the patient to be at low risk of suffering or developing SIRS or sepsis.

5. The method according to any one of 1 to 4, wherein the reference level is obtained by multiplying a baseline level of IL-6 or a variant thereof by a factor of at least about 50, preferably by a factor of at least about 100, more preferably by a factor of at least about 500, most preferably by a factor of at least about 1000.

6. The method of any one of 1 to 5, wherein IL-6 is an IL-6 which can be bound by murine anti-IL-6 monoclonal antibody M-BE8 or M-23C7.

7. The method of any one of 1 to 6, wherein the a level of IL-6 or a variant thereof in the sample is determined by
  i) an antibody which binds to IL-6, or by a fragment or variant thereof;
  ii) an antibody which specifically binds to IL-6, or a fragment or variant thereof;
  iii) an antibody which binds to IL-6 which can be bound by murine anti-IL-6 monoclonal antibody M-BE8 or M-23C7, or by a fragment, or variant thereof; or
  iv) a murine anti-IL-6 monoclonal antibody M-BE8 or M-23C7, or by a fragment or variant thereof.

8. The method of any one of 1 to 7, wherein CRP is determined instead of IL-6 and the method is used to diagnose SIRS or sepsis.

9. The method of any one of 1 to 8, wherein the asymptomatic patient is a patient selected from the group of a trauma patient, a patient with burns, a patient undergoing an treatment, a patient undergoing an invasive treatment, a patient undergoing a surgical intervention.

10. The method of 9, wherein the patient is undergoing an invasive treatment and the sample is taken at least once before the treatment and at least once after the treatment.

11. The method according to any one of 1 to 10, wherein the method
    i) further comprises a step of collecting a sample from the patient by a minimal-invasive step,
    ii) excludes a surgical step of collecting a sample, or
    iii) is an in vitro method.

12. A method of monitoring an asymptomatic patient for the onset of SIRS or for assessing the risk to develop or suffer from SIRS, comprising the steps of
    a) determining the level of IL-6 or a variant thereof in a sample from the patient;
    b) comparing the level of IL-6 or a variant thereof determined in step a) to a reference level; and
    c) recommending, deciding on, initiating, continuing, modulating or discontinuing a SIRS therapy for the patient based on comparison in step b).

13. The method of 12 wherein said reference level said reference level is calculated by multiplying the IL-6 baseline level by a factor of at least 50, said baseline level being obtained (i) when the patient presents to the physician, the emergency unit, the hospital, the intensive care unit, the surgeon or the anaesthesiologist (ii) before and the therapy is initiated, (iii) during the therapy, and/or (iv) after the treatment has been completed.

14. The method of any of 1-13 wherein the IL-6 or variant thereof has a sequence identity to the human IL-6 molecule of at least 80% over the entire length of the human IL-6.

15. A kit adapted for carrying out the method of any of 1 to 14, comprising:
    i) a means for determining the level of IL-6 or a variant thereof;
    ii) a means for comparing the determined level of IL-6 or a variant thereof with reference levels; and optionally
    iii) an instruction for carrying out the method.

16. Use of a means for detecting IL-6 or a variant thereof in a sample of an asymptomatic patient, for early detecting or diagnosing the risk to develop or suffer from SIRS or sepsis, or for early detecting or diagnosing SIRS or sepsis.

17. Use of an increase of the IL-6 level or the level of a variant thereof having a sequence identity to the human IL-6 molecule of at least 80% over the entire length of the human IL-6 over time in samples from an asymptomatic patient isolated at least 2 times at short intervals ranging from 15 minutes+/−20% to 12 hours+/−20% for early detecting or diagnosing the risk to develop or suffer from SIRS or sepsis, or for early detecting or diagnosing SIRS or sepsis.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Patient Characteristics 48 patients, (36 males and 12 females), were included into the study. The mean age of the patients was 61 years, ranging from 19 to 87. All patients were admitted to a thoracic surgical division of the Medizinische Universitat Graz, Austria, for elective surgery. 37 patients underwent lung surgery due to various carcinoma types, 9 patients had oesophagoectomy because of an oesophagus carcinoma, 1 patient underwent gastrectomy, and 1 patient underwent gastrectomy plus oesophagoectomy due to chemical burn. In all patients an antibiotic treatment was initiated in the morning of the day of surgery. All patients had two baseline level measurements before surgery to determine, both, IL-6 and routine laboratory parameters.

Systemic Inflammatory Response Syndrome (SIRS) was diagnosed based on the ACCP/SCCM Consensus Conference Definitions (1992/2003), i.e. a SIRS diagnosed patients displayed at least 2 symptoms of the following:
    a) white blood cell count of more than about 12,000/μ/L or less than about 4000/μ/L;
    b) a body temperature of more than about 38° C. or less than about 36° C.;
    c) a heart rate of more than about 90 beats/minute or a partial pressure of $CO_2$ of less than about 32 mm Hg;
    d) a respiratory rate of more than about 20 breaths/minute; and
    e) more than about 10% immature white blood cells among the counted white blood cells.

Out of the 48 patients 10 (21%) developed SIRS within the time window of monitoring of the study. Out of the 10 patients showing clinical signs of SIRS, three had in addition a positive blood culture which confirmed sepsis. Two of the cases responded to a change of antibiotic treatment though only in one patient the infection was confirmed by a positive blood culture. 5 out of the 10 patients showed purely SIRS signs without infection during the study period. One of the patients developed SIRS shortly after the end of the window of monitoring. In light of the results discussed below this shows that IL-6 based diagnosis and prediction is not limited to sepsis but is also applicable to SIRS.

Material and Methods

IL-6 was determined using a sandwich ELISA immunoassay based on the Roche Cobas Elecsys IL-6 assay (Roche, Mannheim, Germany). In brief, 30.mu.L of the plasma or serum sample were incubated with a biotinylated monoclonal IL-6-specific antibody. After addition of a monoclonal IL-6-specific antibody labeled with a ruthenium complex and streptavidin-coated microparticles, the antibodies formed a sandwich complex with the antigen of the sample. The reaction mixture was then aspirated into the measuring cell of the Elecsys electrochemiluminescence device where the microparticles were magnetically captured onto the surface of the electrode. Unbound substances were then removed with ProCell.

Application of a voltage to the electrode then induced chemiluminescent emission which was measured by a photomultiplier. Results were determined via a calibration curve which was instrument-specifically generated by 2-point calibration and a master curve provided via the reagent barcode. The determined IL-6 concentration was statistically analyzed using standard statistical tests.

According to the study protocol the enrolled patients were monitored regarding clinical and laboratory signs of SIRS starting with 2 baseline levels taken at two time points before and during surgery. After surgery, the patients were surveyed closely by taking blood samples twice before, and every 6 hours during, 6 days after surgery. At every time point when blood was taken the clinical status was recorded according to the established SIRS and sepsis criteria.

Results

Figure 1C:
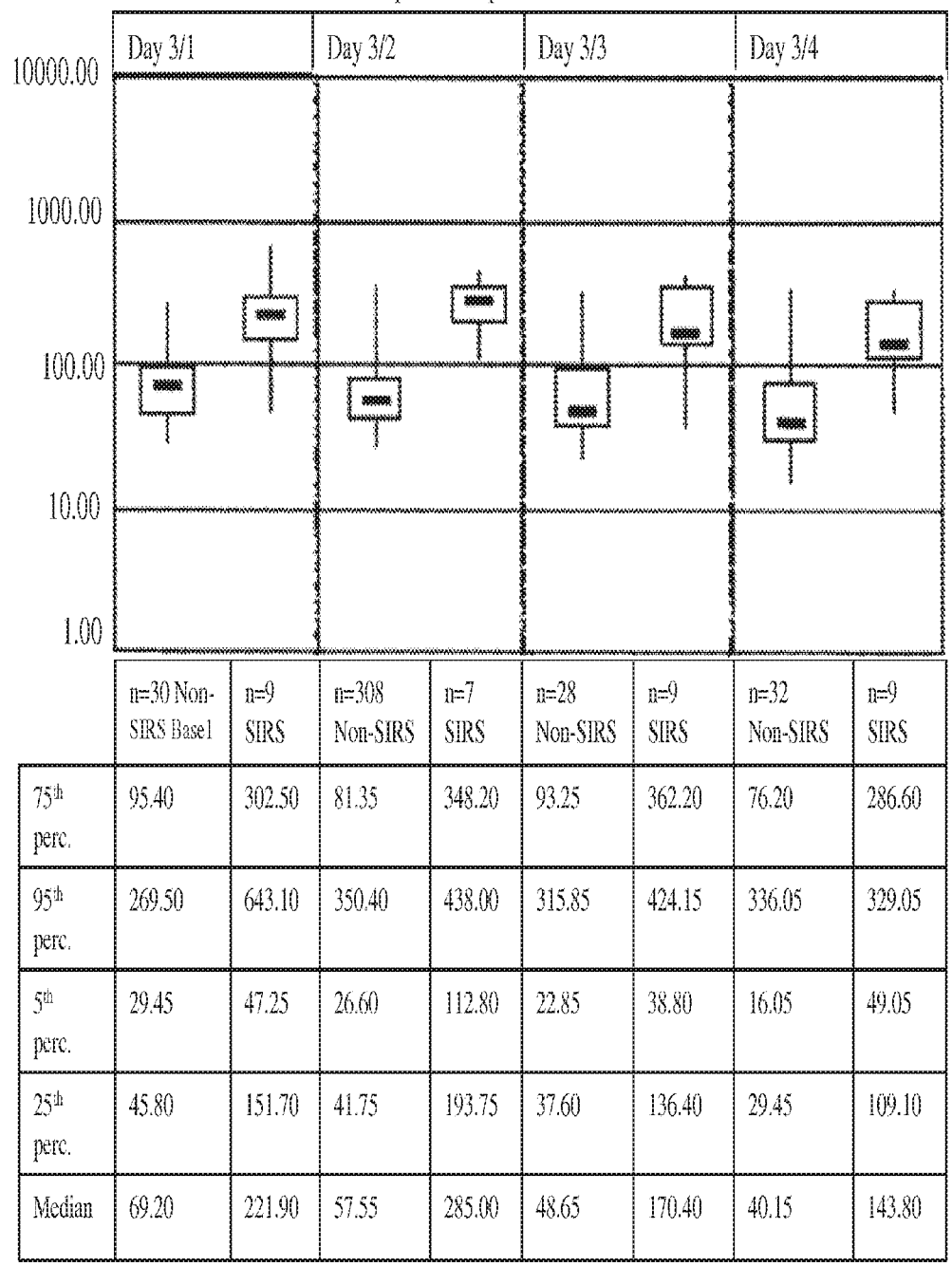
Figure 1D:
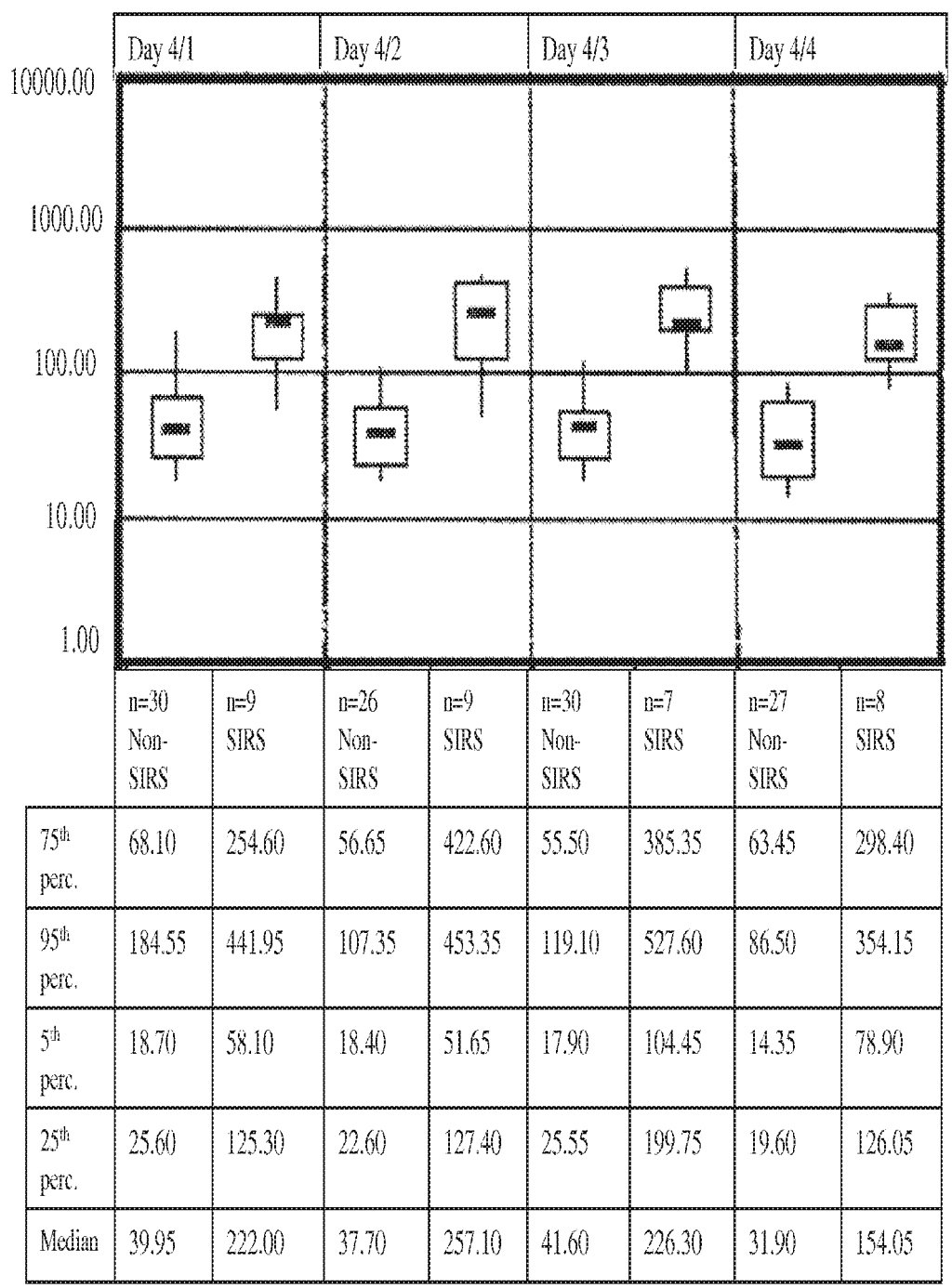
Figure 1E:
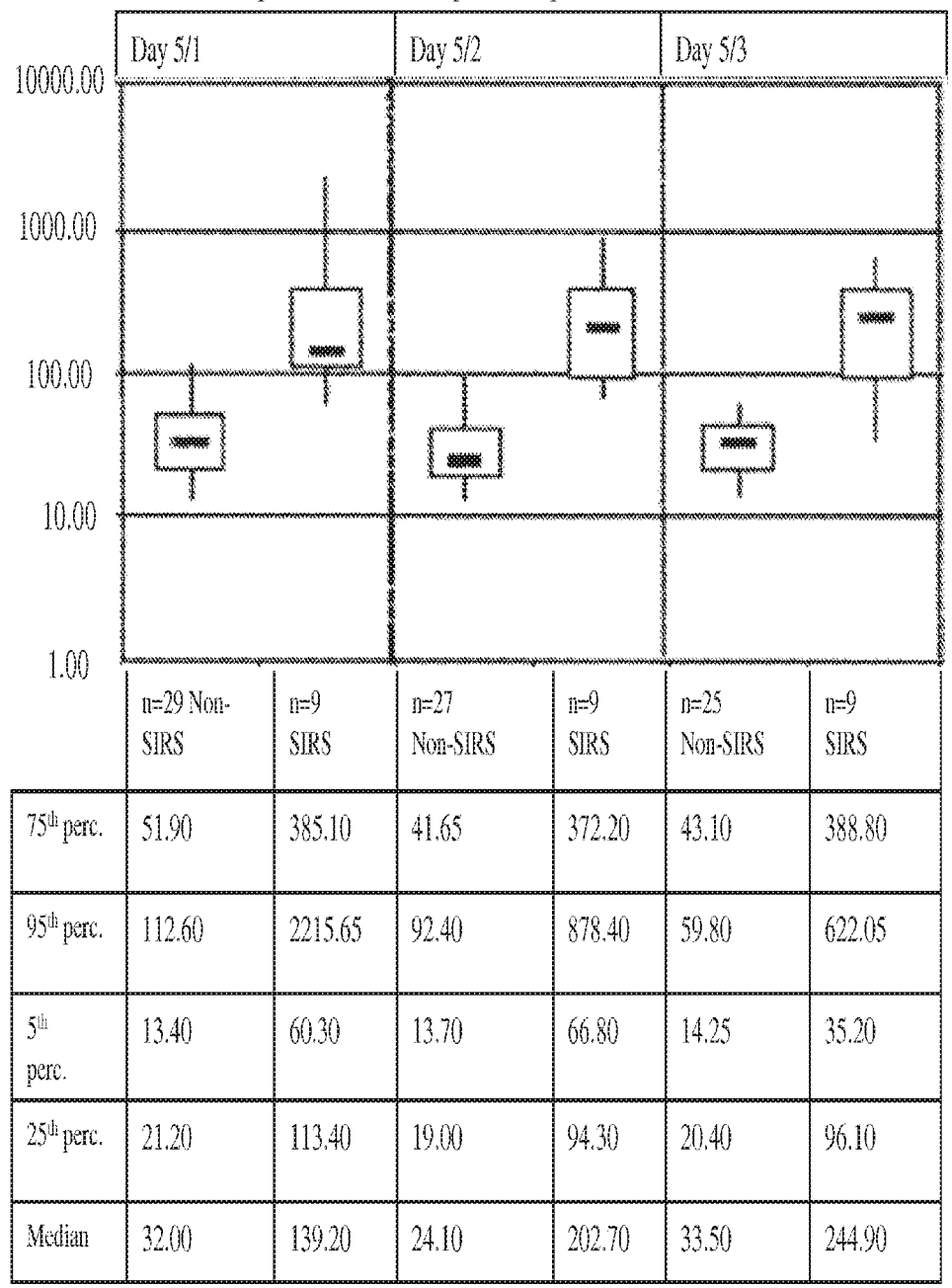
Figure 1F:
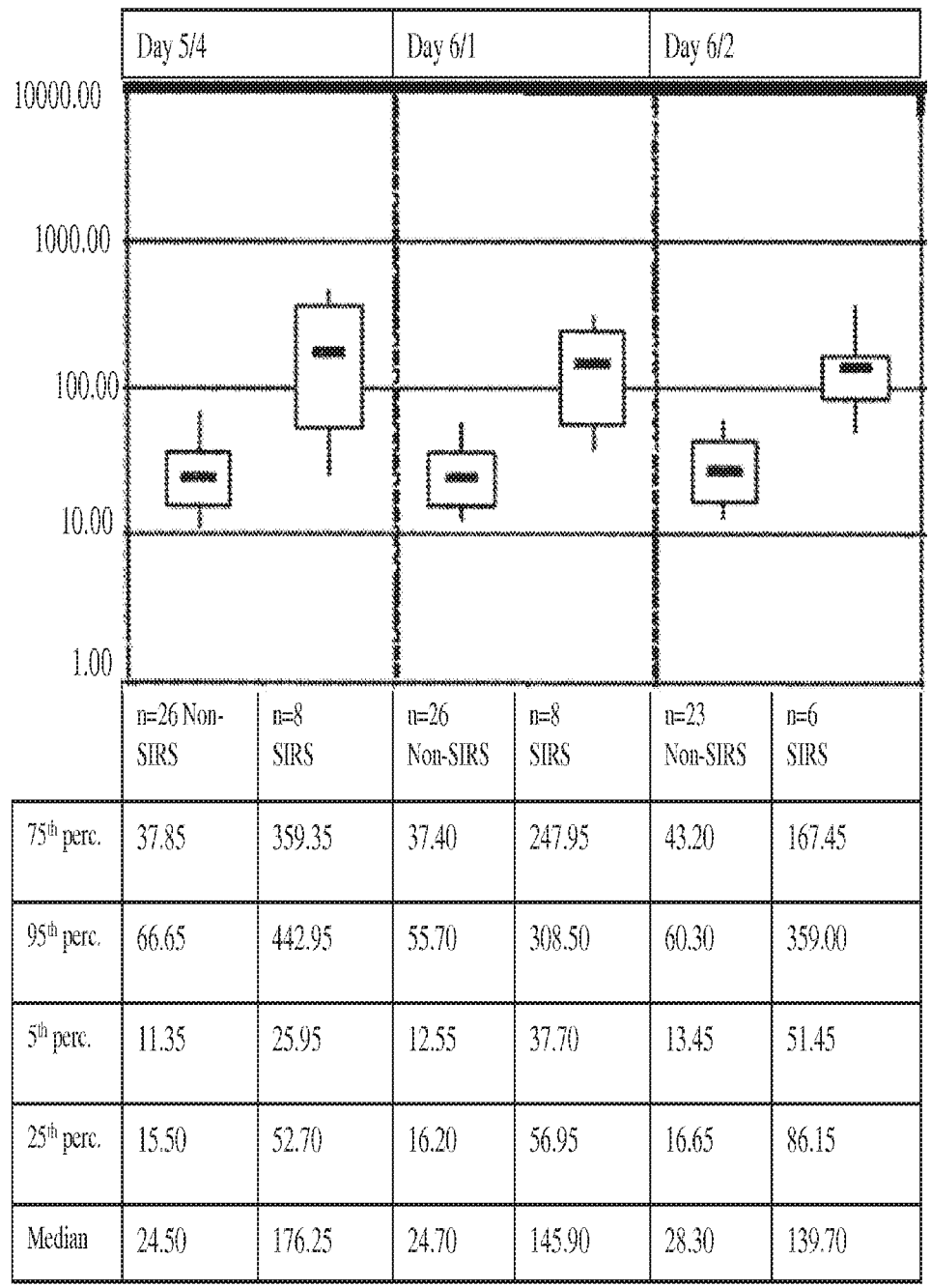
Figure 2B:
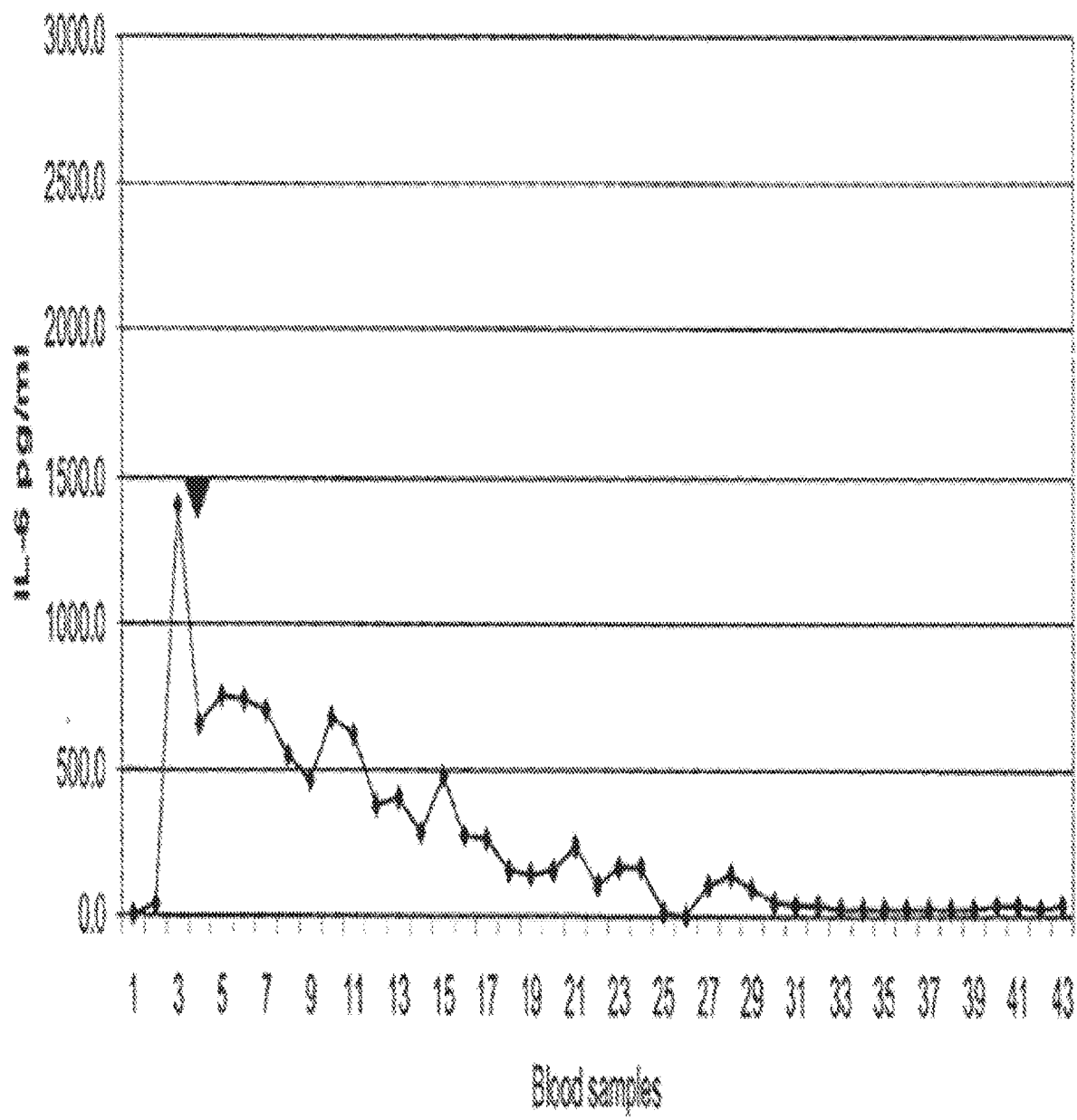
FIG. 2b is a graph presenting the concentration of IL-6 (pg/ml) plotted over time for SIRS patient No. 2 (with the darkened triangle indicating the time point clinical SIRS signs were diagnosed).
Figure 2C:
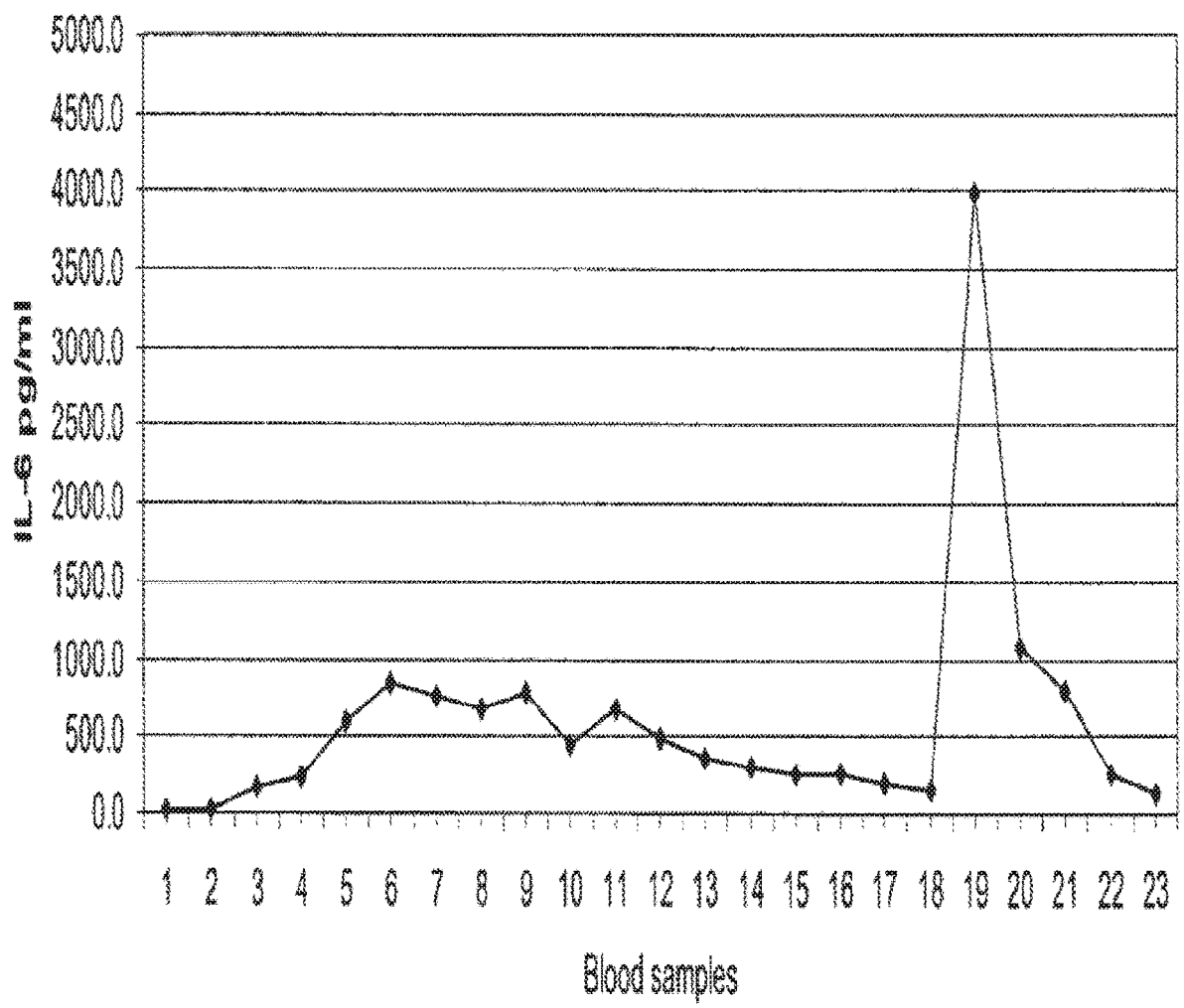
FIG. 2c is a graph presenting the concentration of IL-6 (pg/ml) plotted over time for SIRS patient No. 3.
Figure 2G:
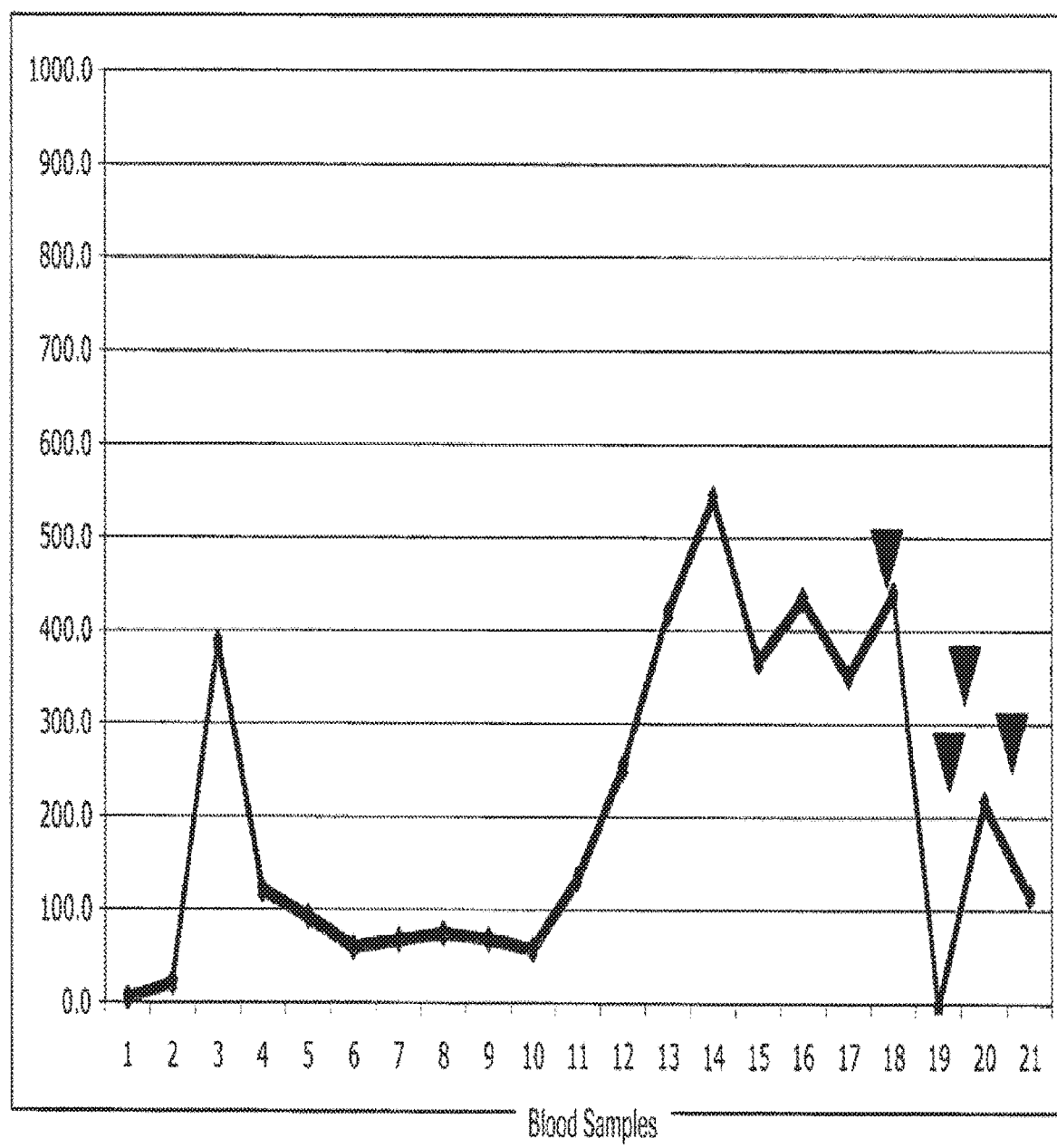
FIG. 2g is a graph presenting the concentration of IL-6 (pg/ml) plotted over time for SIRS patient No. 7 (with the darkened triangle indicating the time point clinical SIRS signs were diagnosed).
Figure 4A:
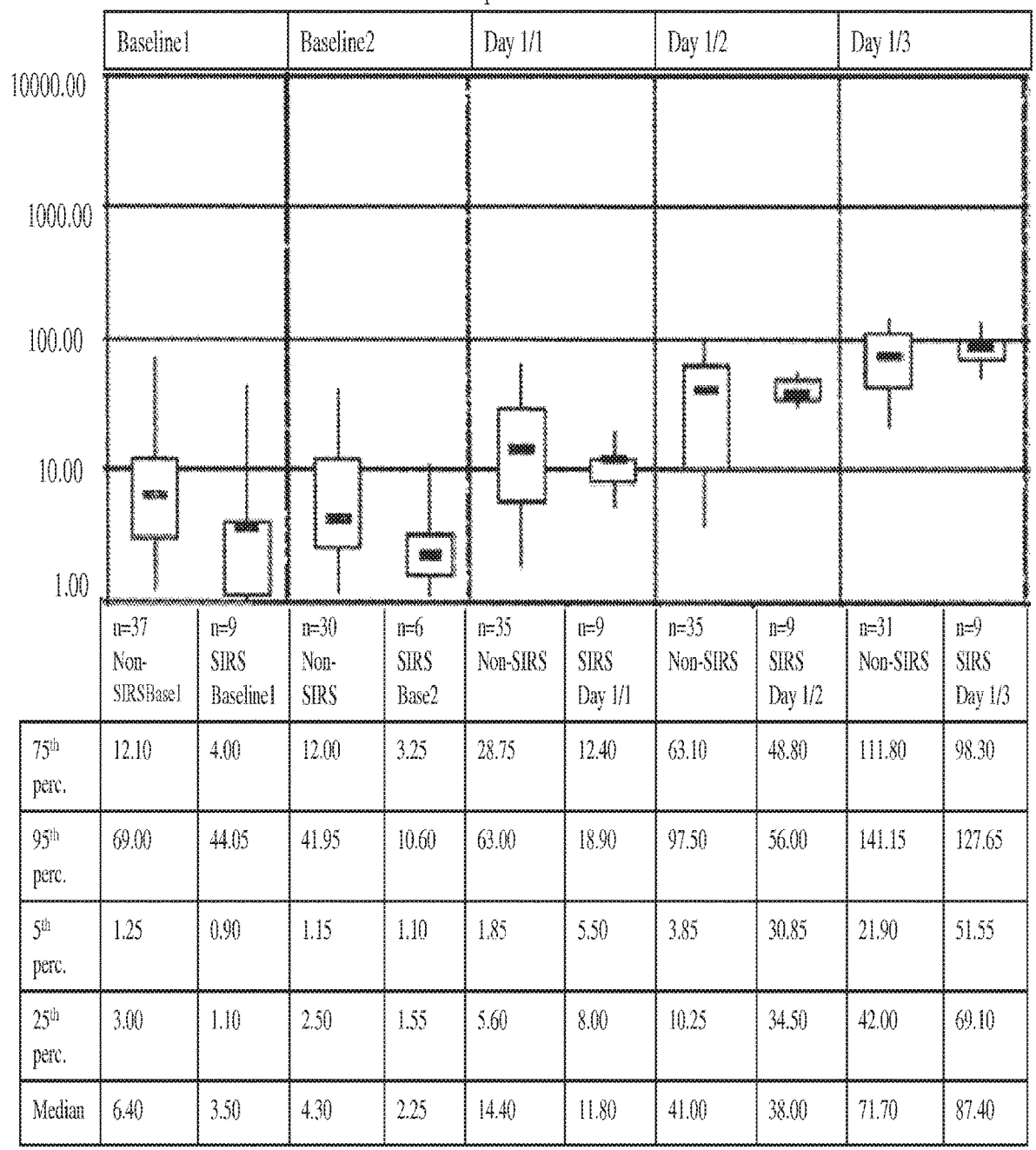
FIGS. 4a-4d are a graph presenting CRP (mg/L) kinetics in asymptomatic patients pre- and post-surgery showing a comparison between pooled patients who developed SIRS/sepsis and those who did not (having CRP levels plotted for baseline 1 (pre-surgery), baseline 2 (during surgery), and post-surgery (day 1, 2, 3 and 4 in which samples were taken at 6 hour intervals) and having Median and the percentiles indicated).
Figure 4B:
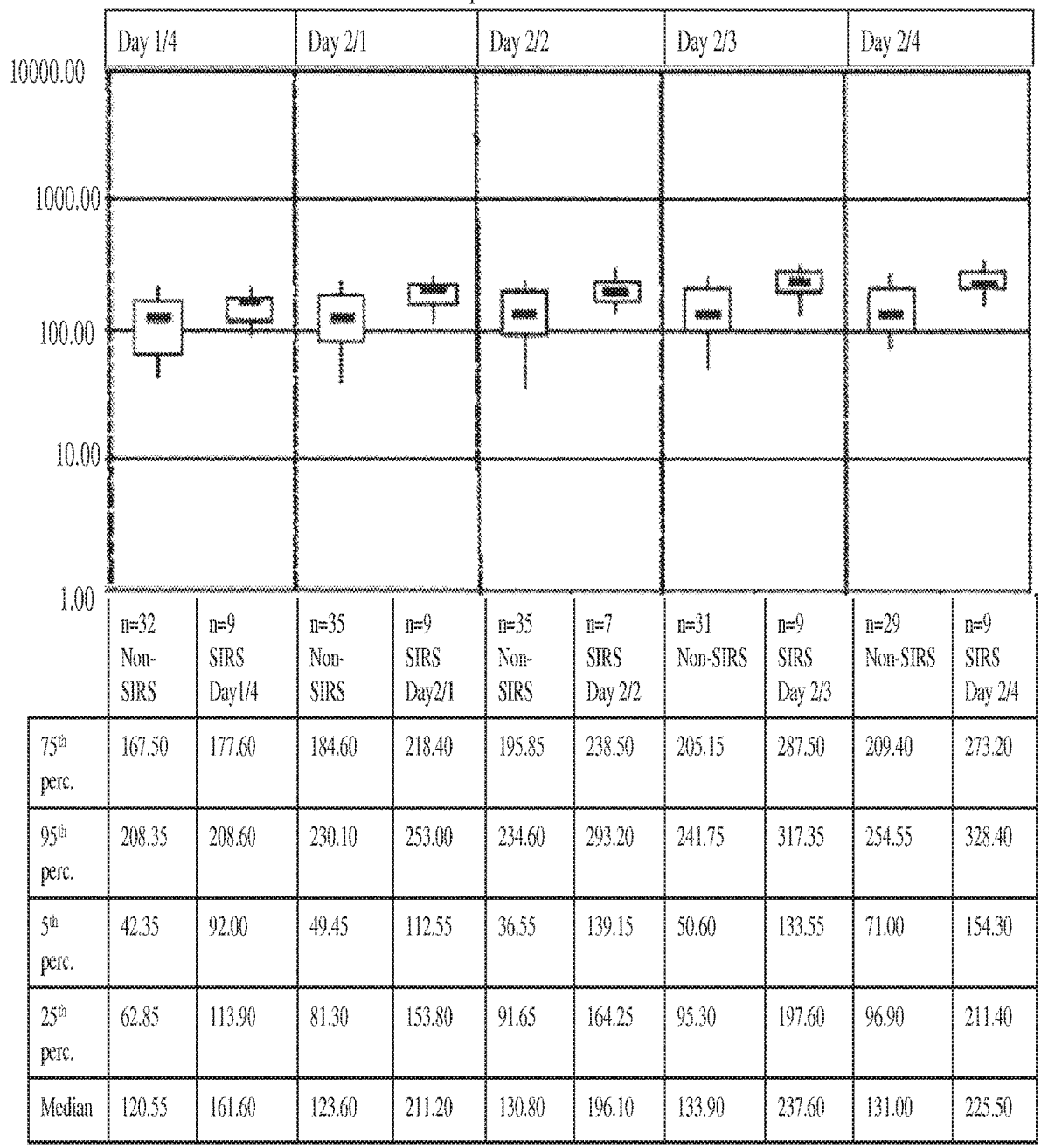
Figure 4C:
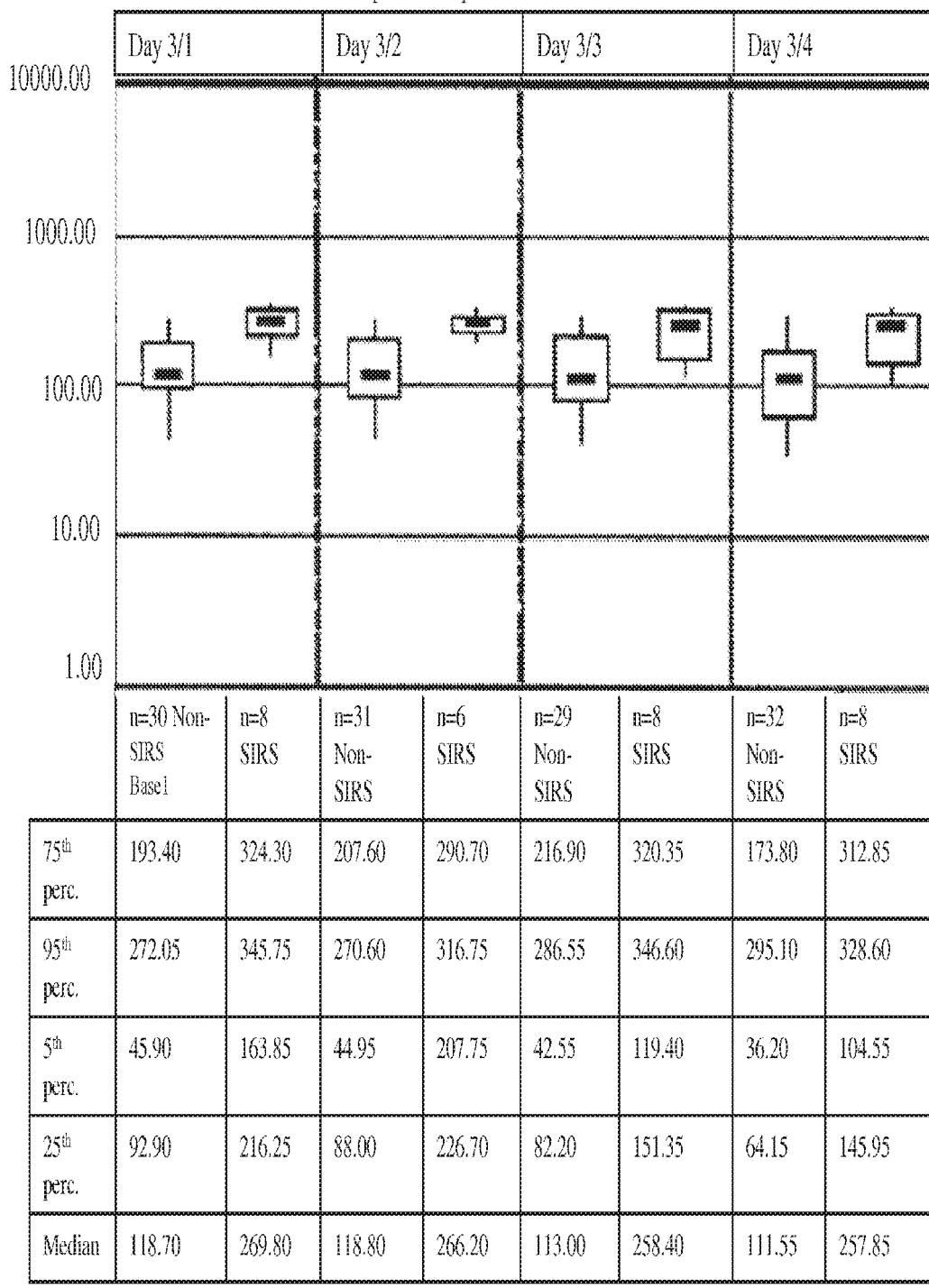
Figure 4D:
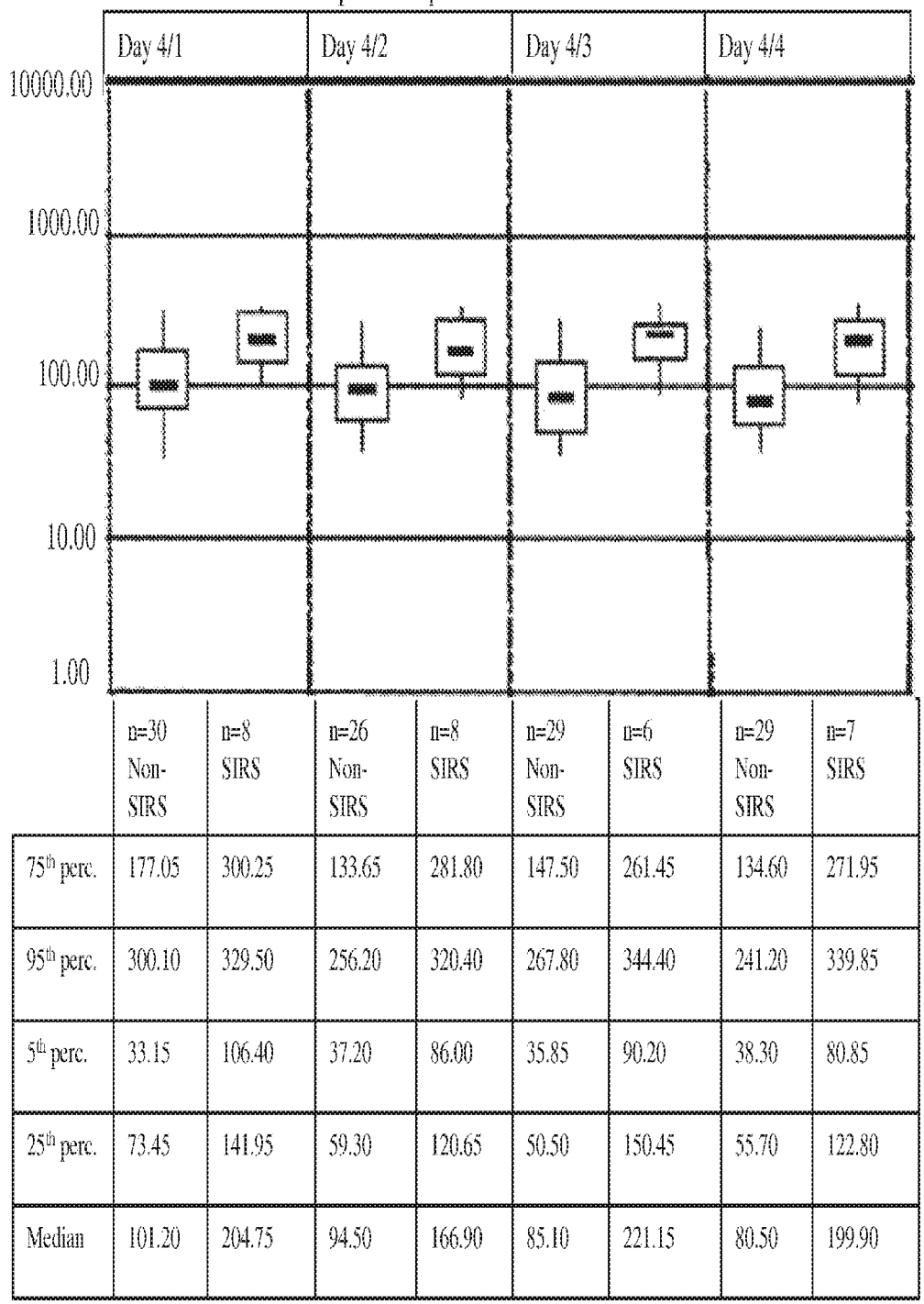
Figure 5A:
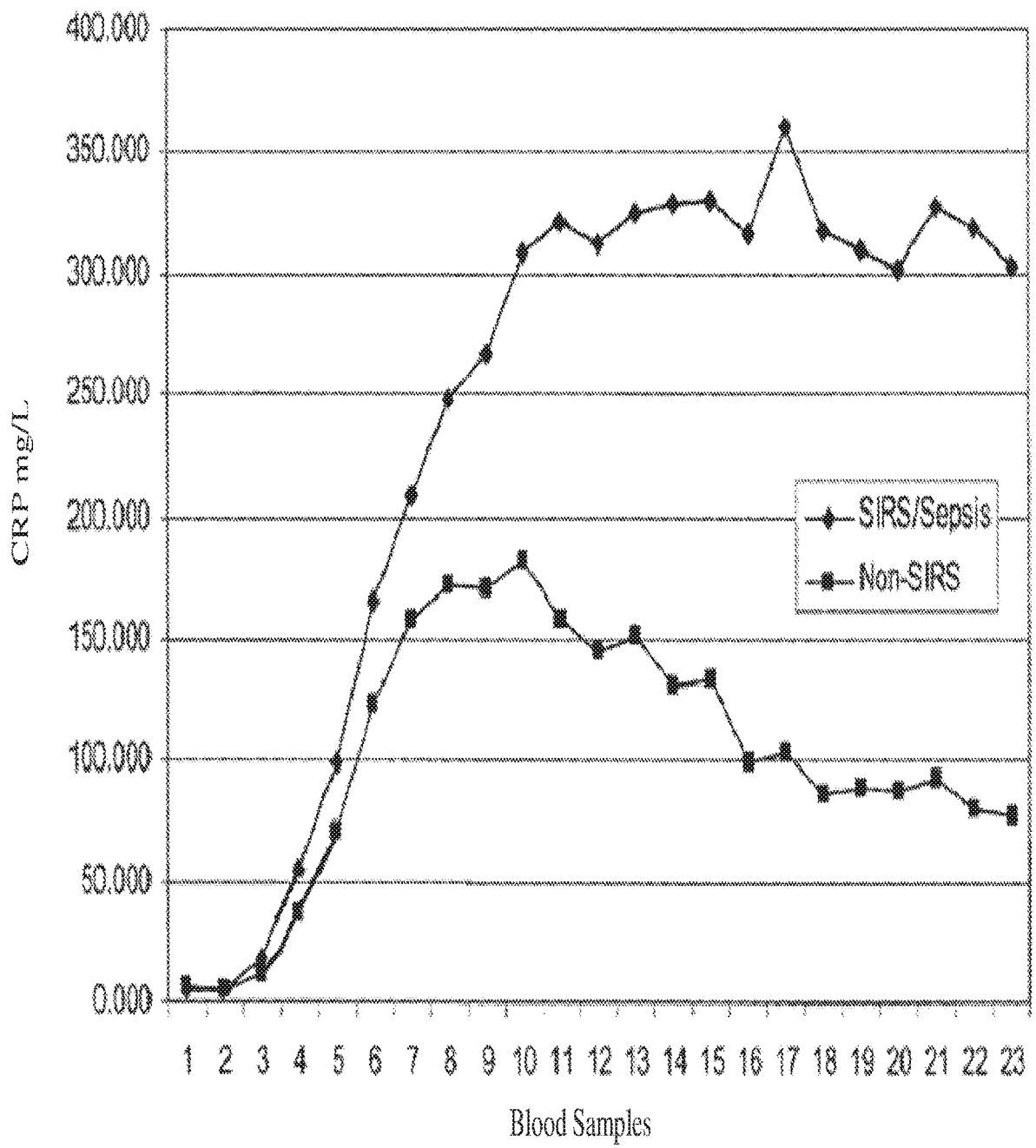
FIG. 5a is a graph presenting a comparison of the CRP kinetics (mg/L) between pooled patients who developed SIRS/sepsis and those who did not (based on asymptomatic patients pre- and post-surgery).
Figure 5B:
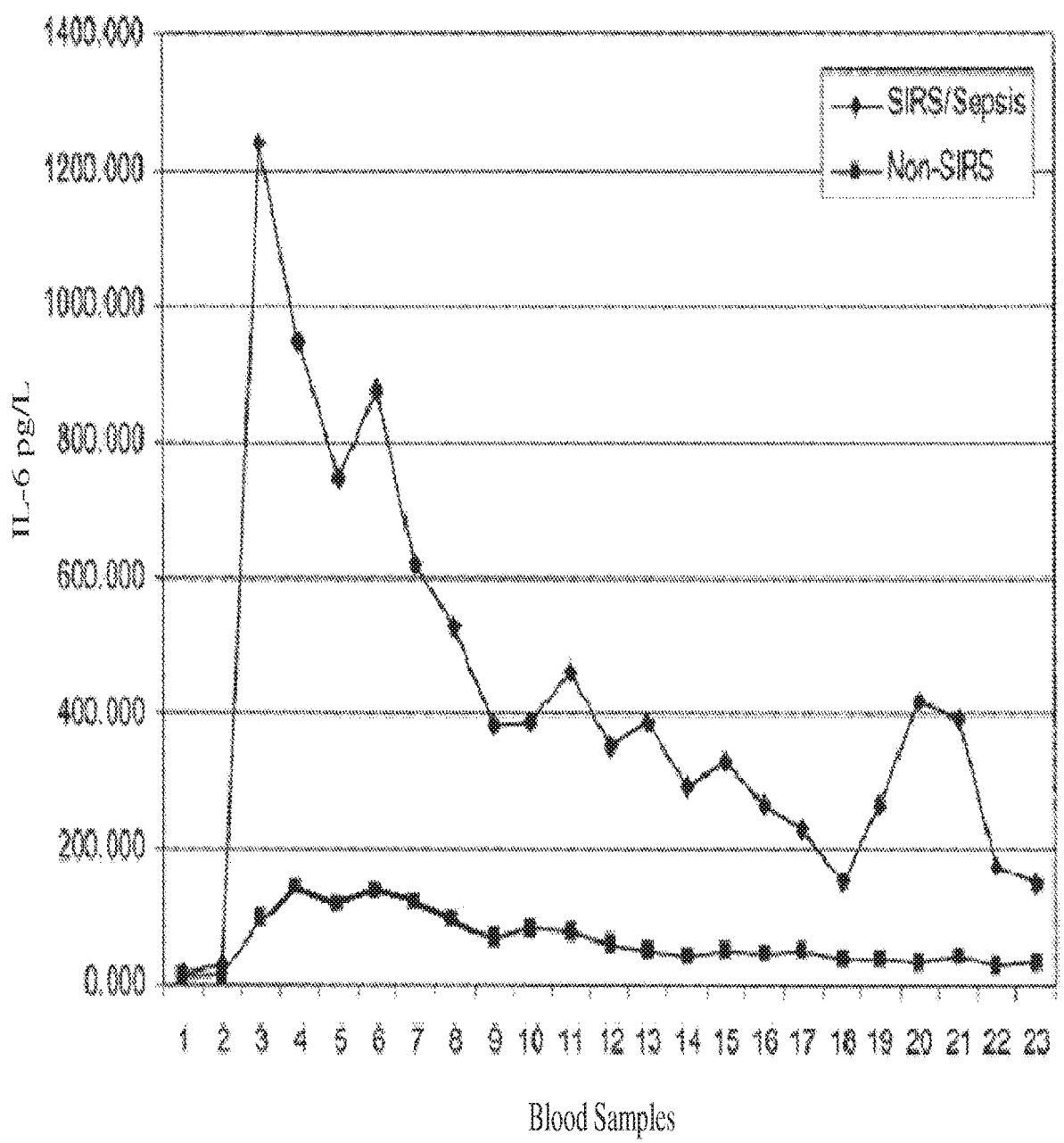
FIG. 5b is a graph presenting a comparison of the IL-6 kinetics (pg/ml) between pooled patients who developed SIRS/sepsis and those who did not (based on asymptomatic patients pre- and post-surgery).

Surprisingly, the IL-6 concentration values of the SIRS/sepsis patients differed significantly from the median values of the patients who did not develop SIRS. Even though the IL-6 levels increased in all patients after surgery, only the patients of the SIRS group displayed a large increase in IL-6 concentration relative to their respective baseline levels, whereas the non-SIRS patients showed only an increase in IL-6 concentration by up to 10-fold when compared to the respective baseline levels (See, in general, the FIGS. 1-5).

Characteristics of some of the SIRS patients (see FIGS. 1 and 2) were as follows:

Patient No. 1: male, age 62, oesophageal carcinoma, oesophagectomy. Routine laboratory parameters and IL-6 values before surgery were inconspicuous (IL-6 baseline levels 14.3 and 2.9 pg/ml). On the first day after surgery a baseline level of 6.4 pg/ml IL-6 was measured at noon. The IL-6 level 6 hours later was 2.279.00 pg/ml. Though the values were decreasing over time, they stayed high until day 6 with values around 500 pg/ml. Clinical SIRS/sepsis signs were only recognized first time on day 4, when a positive blood culture indicating a bacterial infection and an increased body temperature>38° C. was documented. On day 6 the heart rate was >90 beats/minute. This case demonstrates close and frequent IL-6 monitoring allows for early diagnosis and detection of a high risk to develop, or suffer from SIRS, well ahead of the onset of clinical signs and symptoms supporting a diagnosis of SIRS or sepsis.

Patient No. 2: male, age 81, carcinoma at the esophagogastric junction. Before surgery the patient had a low leucocyte count. The second baseline level was actually<4000 white blood cells. On day 1 after surgery the patient had a body temperature of <36° C. and a breathing rate of >20/minute. The two signs were taken as suggestive of SIRS. At the same time the IL-6 values which were at baseline 1, 1.6 pg/ml, and at baseline 2, 37.9 pg/ml, increased to 1400.00 pg/ml. Apart from the blood cell count, which was increased to >12 from day 2 until day 6, only the IL-6 values remained high (up to 500 pg/ml) until day 4 and then slowly decreased. No positive blood culture result was obtained, i.e. no sepsis relevant infection was detected. This case demonstrates that a level of IL-6 above the reference level allows for early diagnosis and detection of a high risk to develop or suffer from SIRS.

Patient No. 3: male, age 70, lung cancer, pneumonectomy. The patient had initially (baseline 1) an increased white blood cell count of >12,000 but a normalized value at baseline 2 time point one week later. The baseline IL-6 levels were also within the normal range of 23.5 and 16.5 pg/ml. During all time points after surgery no clinical signs other than an elevated IL-6 level appeared which pointed to SIRS or sepsis. After day 2 the white blood cell count increased to levels of about 13,000 and did not decrease. IL-6 increased after surgery to values of 200 to 300 pg/ml with interim peaks of 600 pg/ml and even 850 pg/ml at one measuring point. On day 5 in the evening the IL-6 value suddenly increased to 3994.00 pg/ml, following a value of 148.6 pg/ml obtained 6 hours earlier. Two days later, beyond the study protocol time line, the patient developed SIRS criteria and developed a critical condition but could be stabilized. No other laboratory or clinical parameter beside IL-6 had reflected the acute worsening of the patient. Accordingly, the tight monitoring of IL-6 surprisingly allowed for an early detection of a high risk to develop SIRS or sepsis which allowed for an early therapeutic intervention.

Patient No. 4: female, age 50, chondrosarcoma, metastases in the lung, pneumonectomy. The WBC count at baseline, and during the entire study period of 6 days, was in the normal range with a maximum value of 11,000 at day 4. IL-6 increased during surgery (baseline 2) to a value of 282.7 pg/ml. At the first measurement after surgery (day 1/1), IL-6 increased to 1079 pg/ml and 6 hours later peaked at 2771 pg/ml. From that time point on, the values decreased continuously to values of about 70 pg/ml at the end of the study period. SIRS criteria (body temperature>38° C. and HR>90/min) appeared in this patient at the same time points as IL-6 had its highest values which confirms that IL-6 is a reliable early marker of SIRS.

Patient No. 5: male, 19 years, chemical burn of oesophagus and stomach. At baseline before surgery all parameter were in a normal range. IL-6 increased slightly up to 67.4 pg/ml during surgery when the second baseline blood sample was taken. The next blood sample taken 6 hours later (day1/1) already showed an IL-6 value of more than 700 pg/ml which further increased to more than 1000 pg/ml during the next days (day 1/1-3/1). Clinical signs of SIRS (heart rate>100/min and breath rate>20/min) were registered from day 5/2 until the end of the study period (day 6/2).

Patient No. 6: female, 60 years old, lobectomy after lung cancer. At both baseline levels all parameter were in the normal range. The first IL-6 value after surgery (day 1/1) showed a rise to almost 500 pg/ml. IL-6 levels increased over the full study period showing levels between 550 and 150 pg/ml. Leucocytes increased significantly and reached levels of >20.times.10 from day 1/4 on, in conjunction with an increase in body temperature (>38° C.), whereby SIRS was registered. After two time points body temperature returned to normal again but increased once more at day 6/2.

Patient No. 7: male, age 48 years, lung cancer, pneumectomy. Initially, at baseline all parameters were within a normal range. At the second baseline time point, the patient showed an increased heart rate of >100/min which persisted in nearly all study time points. IL-6 increased significantly at day 1/1 to a value of almost 400 pg/ml and fell afterwards to moderately increased values of around 70 pg/ml over the next 7 sampling time points. At day 4/1 IL-6 started to increase again reaching values of more than 500 pg/ml. Clinical signs of SIRS (heart rate>100/min and breath rate>20/min) were registered from day 5/2 until the study end at day 6/2.

Characteristics of some of the non-SIRS patients (See FIGS. 1 and 3-5) were as follows:

38 out of the 48 patients who did not develop SIRS or sepsis, according to the definitions, displayed at least a single symptom of SIRS during the observation period but never displayed two or more, and accordingly these patients were diagnosed as not suffering from SIRS. The baseline IL-6 values were (of non-SIRS patients) were comparable to the baseline values of the SIRS patients. After surgery all non-SIRS patients also had a slight increase in the IL-6, values some up to about 100 pg/ml, some up to 400, one with a single peak of 900 pg/ml, but they did not show the drastic elevation of IL-6 levels observed in the SIRS patient group. The observed small increase in IL-6 levels in the non-SIRS patients is within the range that one would expect, considering the severeness of the conducted surgery. Based on the outcome (no onset of SIRS or sepsis) in these patients, the data demonstrate that the patients were at a low risk to suffer or develop SIRS or sepsis.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

The invention claimed is:

1. A method of diagnosis of a risk to develop a systemic inflammatory response syndrome (SIRS) or sepsis in an asymptomatic human patient after an invasive treatment, the method comprising:

detecting a first concentration of IL-6 by contacting in a first step of contacting, in vitro, a portion of a first sample selected from the group consisting of: serum, plasma and blood, with an antibody having specific binding affinity for IL-6, the first sample obtained from the human patient asymptomatic for SIRS or sepsis prior to the invasive treatment;

multiplying the concentration of IL-6 in the first sample by a factor of at least 50 to establish a reference IL-6 level;

detecting at least a second concentration of IL-6 by contacting in at least one second step of contacting, in vitro, a portion of at least a second sample selected from the group consisting of serum, plasma and blood with an antibody having specific binding affinity for IL-6, wherein the at least one second sample is obtained from the human patient asymptomatic for SIRS at intervals ranging from 15 minutes to 12 hours for a period of 3 to 10 days after the invasive treatment;

comparing the reference IL-6 level with the concentration of IL-6 calculated in the at least one second sample; and identifying the human patient as at risk of developing SIRS or sepsis when the concentration of IL-6 in the at least one second sample is higher than the reference IL-6 level; and administering to the human patient identified as at risk of developing SIRS or sepsis at least one of a broad spectrum antibiotic treatment, a change of pre-existent antibiotic treatment to a more efficient one, and an antifungal treatment.

2. The method of claim 1, wherein the antibody is selected from the group consisting of M-BE8 and M-23C7.

3. The method of claim 1, wherein the patient asymptomatic for SIRS having undergone an invasive treatment is a cancer patient.

4. The method of claim 1, wherein at least the second sample is obtained from the human patient asymptomatic for SIRS at regular intervals following the invasive treatment, the intervals ranging from 1 hour+/−20% to 3 hours+/−20%.

5. The method of claim 1 further comprising detecting if the patient has infection by a blood culture.

6. The method of claim 1 further comprising subjecting the human patient identified as at risk of developing SIRS or sepsis to at least one monitoring means selected from the group consisting of endoscopic controls, radiological ultrasound, chest roentgenograms and CT-scans before the step of administering treatment to the human patient identified at risk.

* * * * *

SEQUENCE LISTING

```
<160> NUMBER OF SEQ ID NOS: 1

<210> SEQ ID NO 1
<211> LENGTH: 212
<212> TYPE: PRT
<213> ORGANISM: Homo sapiens

<400> SEQUENCE: 1

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```